(12) United States Patent
Park et al.

(10) Patent No.: US 9,044,755 B2
(45) Date of Patent: Jun. 2, 2015

(54) GENE ANALYSIS APPARATUS AND GENE ANALYSIS METHOD USING THE SAME

(75) Inventors: Chin-sung Park, Yongin-si (KR); Won-jong Jung, Seongnam-si (KR); Joon-ho Kim, Seongnam-si (KR); Kak Namkoong, Seoul (KR); Kyu-youn Hwang, Yongin-si (KR); Won-seok Chung, Suwon-si (KR); Hee-kyun Lim, Hwaseong-si (KR); Sung-hong Kwon, Yongin-si (KR); Sun-ok Jung, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 36 days.

(21) Appl. No.: 13/176,777

(22) Filed: Jul. 6, 2011

(65) Prior Publication Data
US 2012/0141999 A1 Jun. 7, 2012

(30) Foreign Application Priority Data
Dec. 7, 2010 (KR) ........................ 10-2010-0124231

(51) Int. Cl.
*C12Q 1/68* (2006.01)
*G01N 21/75* (2006.01)
*B01L 7/00* (2006.01)
*B01L 3/00* (2006.01)

(52) U.S. Cl.
CPC . *B01L 7/52* (2013.01); *G01N 21/75* (2013.01); *C12Q 1/68* (2013.01); *B01L 3/502715* (2013.01); *B01L 2200/027* (2013.01); *B01L 2200/028* (2013.01); *B01L 2200/04* (2013.01); *B01L 2200/0605* (2013.01); *B01L 2200/0621* (2013.01); *B01L 2200/0684* (2013.01); *B01L 2200/10* (2013.01); *B01L 2200/16* (2013.01); *B01L 2300/0627* (2013.01); *B01L 2300/0816* (2013.01); *B01L 2300/087* (2013.01); *B01L 2300/0874* (2013.01); *B01L 2300/0887* (2013.01); *B01L 2300/18* (2013.01); *B01L 2400/0487* (2013.01); *B01L 2400/06* (2013.01); *B01L 2400/0655* (2013.01)

(58) Field of Classification Search
CPC .................................. C12Q 1/68; G01N 21/75
USPC .............................................. 435/6.1; 422/417
See application file for complete search history.

(56) References Cited

U.S. PATENT DOCUMENTS

| | | | |
|---|---|---|---|
| 7,207,345 B2 * | 4/2007 | Somerville | 137/7 |
| 7,569,127 B1 | 8/2009 | Cho | |
| 7,682,565 B2 * | 3/2010 | Linton et al. | 422/68.1 |
| 2003/0129646 A1 | 7/2003 | Briscoe et al. | |
| 2005/0053952 A1 | 3/2005 | Hong et al. | |
| 2005/0255007 A1 | 11/2005 | Yamada et al. | |
| 2006/0134599 A1 * | 6/2006 | Toner et al. | 435/4 |
| 2009/0060797 A1 | 3/2009 | Mathies et al. | |
| 2009/0236226 A1 | 9/2009 | Yuen | |
| 2009/0253181 A1 | 10/2009 | Vangbo et al. | |
| 2010/0120129 A1 * | 5/2010 | Amshey et al. | 435/270 |
| 2010/0167384 A1 | 7/2010 | Clemmens et al. | |

FOREIGN PATENT DOCUMENTS

EP    2 075 584 A1    7/2009

OTHER PUBLICATIONS

Cheng et al. Applied Physics Letters (2009) 95: 214103 (3 pages).*
Extended European Search Report from the European Patent Office in European Patent Application No. 11181238.4, mailed Mar. 21, 2012.

* cited by examiner

*Primary Examiner* — Ardin Marschel
(74) *Attorney, Agent, or Firm* — Leydig, Voit & Mayer, Ltd.

(57) ABSTRACT

A gene analysis apparatus includes a sample preparation chip in which a polymerase chain reaction ("PCR") sample is prepared, a PCR chip in which a PCR is performed on the PCR sample, and a package layer on which the sample preparation chip and the PCR chip are mounted. The package layer includes a channel through which a material flows from the sample preparation chip to the PCR chip. The sample preparation chip and the PCR chip are on a same side or on opposing sides of the package layer.

18 Claims, 17 Drawing Sheets

GENE ANALYSIS APPARATUS AND GENE ANALYSIS METHOD USING THE SAME

CROSS-REFERENCE TO RELATED APPLICATIONS

This application claims priority to Korean Patent Application No. 10-2010-0124231, filed on Dec. 7, 2010, and all the benefits accruing therefrom under 35 U.S.C. §119, the disclosure of which is incorporated herein in its entirety by reference.

BACKGROUND

1. Field

Provided are biomaterial analysis apparatuses, and in particular, to gene analysis apparatuses and gene analysis methods using the same.

2. Description of the Related Art

Genetic information about a biomaterial is obtained by analyzing a cell contained in the biomaterial. In particular, genetic information about a biomaterial is contained in a nucleic acid of a cell. Various biomaterials are distinguished from each other by obtaining information about a nucleic acid. Accordingly, a biomaterial that causes an unknown biological phenomenon is identifiable.

In order to obtain information about presence or absence of a particular nucleic acid and if present, an amount of the nucleic acid, isolating of a nucleic acid from a cell of a biomaterial including the nucleic acid needs to be performed in advance. Following the isolation, the isolated nucleic acid is amplified so as to increase the amount of the nucleic acid to a level suitable for testing. Isolating of a nucleic acid may be performed using a method using beads. Amplifying of the isolated nucleic acid to identify whether a particular nucleic acid is present and an amount of a nucleic acid may be performed by polymerase chain reaction ("PCR").

However, conventionally, isolating of a nucleic acid and amplifying and testing of the isolated nucleic acid are performed in a separate chip or system. Accordingly, contamination may occur due to an external material between steps. Thus, accuracy or reliability of the obtained results may be reduced.

SUMMARY

Provided are packaged gene analysis apparatuses.

Provided are gene analysis methods using the packaged gene analysis apparatuses.

Additional aspects will be set forth in part in the description which follows and, in part, will be apparent from the description, or may be learned by practice of the presented embodiments.

Provided is a gene analysis apparatus including a sample preparation chip in which a polymerase chain reaction ("PCR") solution sample is prepared, a PCR chip in which a PCR is performed on the PCR solution sample, and a package layer on which the sample preparation chip and the PCR chip are mounted.

The package layer may include a channel through which a material flows from the sample preparation chip to the PCR chip.

The sample preparation chip and the PCR chip may be on a same side or different sides of the package layer.

The package layer may include a main layer, and a cover which covers the main layer.

The package layer may include regions in which a material used to prepare the PCR sample is stored or in which the material flows, and a channel through which the material to the sample preparation chip is supplied.

The channel may include a plurality of sub-channels.

The PCR sample may include a nucleic acid and an amplification reagent.

The nucleic acid may include a nucleic acid derived from one selected from the group consisting of a pathogen, a bacterium, a virus, and a fungus.

The sample preparation chip may includes a bead chamber in which a cell is lysed, a first metering channel in which a PCR mixture is quantified, a second metering channel in which a cell lysis product supplied from the bead chamber is quantified, a mixing channel in which materials contained in the first and second metering channels are mixed, a same microchannel and a same micropump between the first metering channel and the mixing channel and between the second metering channel and the mixing channel, a first channel through which a material flows into the bead chamber and the first metering channel, and a second channel through which a material contained in the mixing channel flows into a channel of the package layer.

The channel may be a vertical or horizontal channel.

Each of the first and second metering channels and the mixing channel may have a predetermined volume and wind.

A bubble trap zone may be at an end of the mixing channel near the channel of the package layer.

According to another aspect of the present invention, a gene analysis method includes preparing a PCR sample, supplying the PCR sample to a PCR chip, and performing PCR on the PCR sample in the PCR chip. All the processes are performed in-situ and not exposed to an outside.

The preparing the PCR solution sample includes lysing a cell, quantifying a cell lysis product, quantifying a PCR mixture, and mixing the quantified cell lysis product and the quantified PCR mixture.

The quantifying a cell lysis product may include opening valves at ends of a metering channel in which the cell lysis product is filled, supplying the cell lysis product to the metering channel in such an amount that an amount of the cell lysis product is greater than a volume of the metering channel, closing the valves at the ends of the metering channel, and discharging the cell lysis product that is outside the metering channel.

The lysing the cell may further include allowing the cell to move periodically or non-periodically.

The quantifying the PCR mixture may include opening valves at ends of a metering channel in which the PCR mixture is filled, supplying the PCR mixture to the metering channel in such an amount that an amount of the PCR mixture is greater than a volume of the metering channel, closing the valves at the ends of the metering channel, and discharging the PCR mixture that is outside the metering channel.

The mixing of the quantified cell lysis product and the quantified PCR mixture may include alternately supplying a portion of the quantified cell lysis product and a portion of the quantified PCR mixture to the mixing channel.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
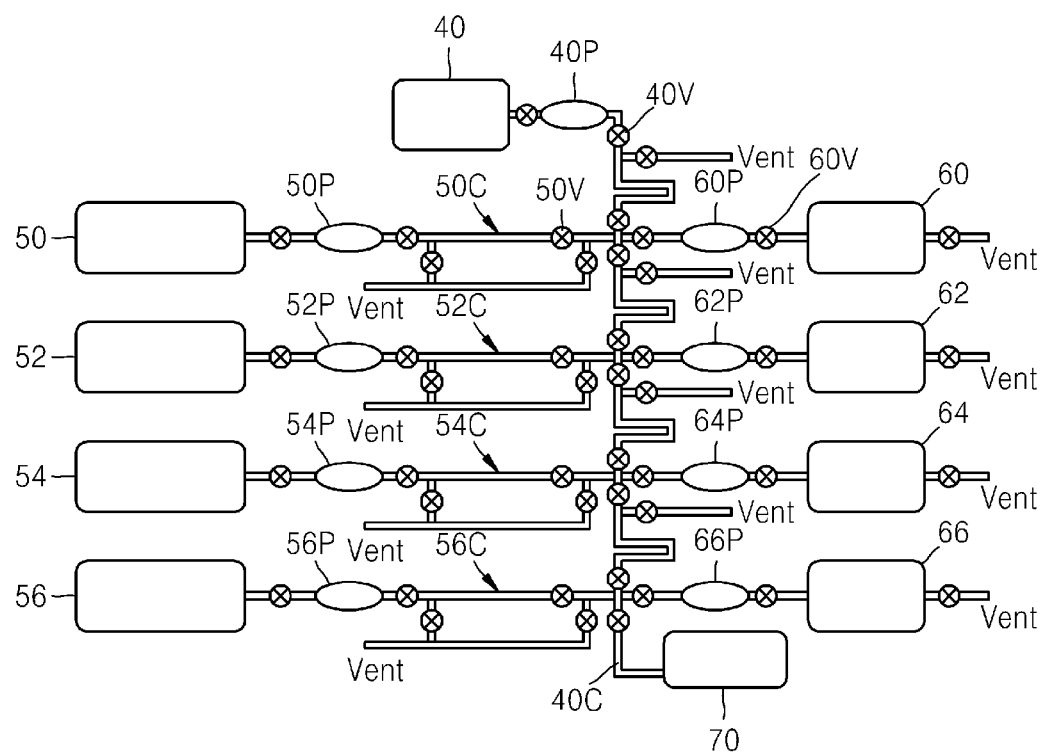
FIG. 1 is a diagram illustrating functional connection relationships among components of a gene analysis apparatus according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, connected may refer to elements being physically and/or fluidly connected to each other. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

Spatially relative terms, such as "lower," "under," "above," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" or "under" relative to other elements or features would then be oriented "upper" and "above" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

First, an embodiment of a gene analysis apparatus according to the present invention will be described in detail.

FIG. 1 is a diagram illustrating functional connection relationships among components of a gene analysis apparatus according to an embodiment of the present invention.

Referring to FIG. 1, the gene analysis apparatus may include a chamber 40 in which a cell is lysed, a pump 40P which pumps a cell lysis product to a microchannel 40C, microchannels 50C, 52C, 54C, and 56C through which polymerase chain reaction ("PCR") mixtures, that is, an amplification reagent, contained in for example, first through fourth PCR mixture chambers 50, 52, 54, and 56 flow respectively to first through fourth PCR chambers 60, 62, 64, and 66 of a PCR chip, pumps 50P, 52P, 54P, and 56P which pump the PCR mixtures contained in first through fourth PCR mixture chambers 50, 52, 54, and 56 to the microchannels 50C, 52C, 54C, and 56C, respectively, pumps 60P, 62P, 64P, and 66P which mix the cell lysis product and PCR mixtures to obtain a PCR solution and inject the solution to the first through fourth PCR chambers 60, 62, 64, and 66, and microvalves 40V, 50V, and 60V which control flow of a fluid flowing through the respective microchannels.

The term "amplification reagent" used herein refers to reagents required for the amplification of a target nucleic acid by PCR. The amplification reagent may include two primers that are complementary to the 3' ends of each of the sense and antisense strand of the target nucleic acid, nucleic acid polymerase, deoxynucleotide triphosphate ("dNTP"), buffer solution, divalent cations such magnesium ions and monovalent cation such as potassium ions. The polymerase may be a thermostable polymerase, for example a Taq polymerase with temperature optimum at around 70 degrees Celsius (° C.). The buffer solution may provide a suitable chemical environment for optimum activity and stability of the DNA polymerase.

A waste chamber 70 may house a discharge generated when the cell lysis product and the PCR mixtures are quantified.

The pumps 40P, 50P, 52P, 54P, 56P 60P, 62P, 64P, and 66P illustrated in FIG. 1 are micropumps, and may be mechanical pumps or non-mechanical pumps. A mechanical micropump may include an actuator and a moving part that is a film or a flap. In this case, a driving force of the mechanical micropump may be generated using a piezoelectric effect, an electrostatic effect, a thermo-pneumatic effect, a pneumatic effect, or a magnetic effect. A non-mechanical micropump may be driven by an electro-hydrodynamic flow, an electro-osmotic flow, or an ultrasonic flow.

A gene analysis apparatus according to an embodiment of the present invention will now be described in detail as follows in terms of structure.

Figure 2:
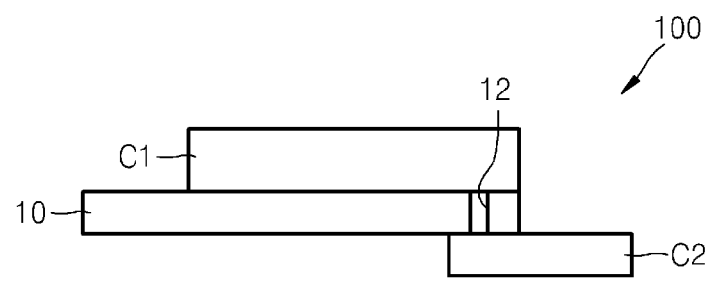
FIG. 2 is a schematic cross-sectional view of a gene analysis apparatus according to an embodiment of the present invention.

FIG. 2 is a schematic cross-sectional view of a gene analysis apparatus 100 according to an embodiment of the present invention.

Referring to FIG. 2, the gene analysis apparatus 100 may include a sample preparation chip C1, a PCR chip C2, and a package layer 10. The package layer 10 is disposed between the sample preparation chip C1 and the PCR chip C2, and includes a channel 12. The channel 12 may include a plurality of sub-channels. The channel 12 may be a hole. Through the channel 12, a fluid flows between the sample preparation chip C1 and the PCR chip C2. The sample preparation chip C1 faces the PCR chip C2 with the package layer 10 between the sample preparation chip C1 and the PCR chip C2. The PCR chip C2 may include a silicon layer and a polymer film having a thickness of about 100 micrometers (μm) or less. Also, the PCR chip C2 may be a chip including a silicon layer and a glass layer, or a chip formed of only a polymer. A silicon layer has higher thermal conductivity than a glass layer. Accordingly, a chamber contained in the PCR chip C2 may mostly include silicon. Also, an upper portion of the chamber of the PCR chip C2 needs to be glass or a transparent polymer, thereby allowing fluorescence detection. A region bonded to the PCR chip C2 may need photo detection in the gene analysis apparatus 100. Also, an optical window may be in the gene analysis apparatus 100 since the chamber of the PCR chip C2 is viewed by using a photo system.

In the sample preparation chip C1, a cell lysis product of a cell in a particular biomaterial is prepared, and the cell lysis product is mixed with a PCR mixture, which is a mixture of an amplification reagent except template nucleic acids. The mixing product flows to the PCR chip C2 through the channel 12 of the package layer 10. In the PCR chip C2, PCR is performed to confirm whether a target nucleic acid is in the cell lysis product, and if a target nucleic acid is present, the target nucleic acid may be amplified, thereby identified.

The cell of the particular biomaterial may be a pathogen, a bacterium, a virus, or a fungus. The cell may be provided as contained in an appropriate liquid medium. Examples of a liquid medium are a cell cultivation medium, a buffer (for example, a phosphate buffered saline ("PBS") buffer), saline, and water. The liquid medium may also be a medium including a cell lysis reagent such a detergent or enzymes degrading the cell.

The channel 12 longitudinally extends in a direction perpendicular to the sample preparation chip C1 and the PCR chip C2, such that the channel 12 is vertically connected to the package layer 10, and directly connected to the sample preparation chip C1 and the PCR chip C2. Accordingly, a length of the channel 12 between the sample preparation chip C1 and the PCR chip C2 may be a minimum distance. When the reaction solution including the isolated nucleic acid and the amplification reagent mixture are supplied to the PCR chip C2, some of the solution remaining in the channel 12 after supplied to the PCR chip C2 is wasted. An amount of the waste solution is proportional to a volume of the channel 12. In other words, the volume of the channel 12 is equivalent to an amount of the waste solution, that is, a dead volume. Since the length of the channel 12 between the sample preparation chip C1 and the PCR chip C2 is a minimum distance, the dead volume of the channel 12 is very small.

Figure 5:
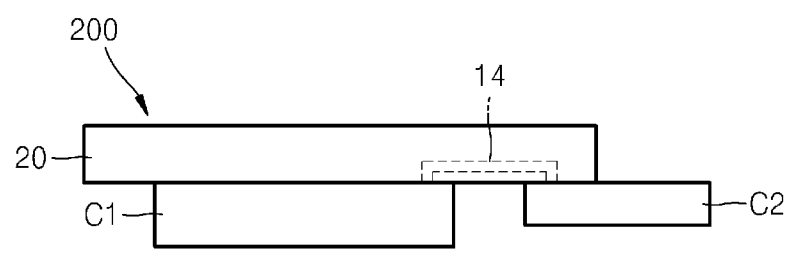
FIG. 5 is a schematic view of a gene analysis apparatus according to another embodiment of the present invention.

As illustrated in FIG. 2, the sample preparation chip C1, the PCR chip C2, and the package layer 10 are packaged by combination. Accordingly, when a gene analysis is performed using the gene analysis apparatus 100 of FIG. 2, all gene analysis processes may be performed in the gene analysis apparatus 100 of FIG. 2 without exposure to the outside. That is, all gene analysis processes may be performed in-situ without exposure to the outside. Like the gene analysis apparatus 100 of FIG. 2, when a gene analysis apparatus 200 of FIG. 5 is used, all gene analysis processes may be performed in-situ without exposure to the outside.

Figure 3:
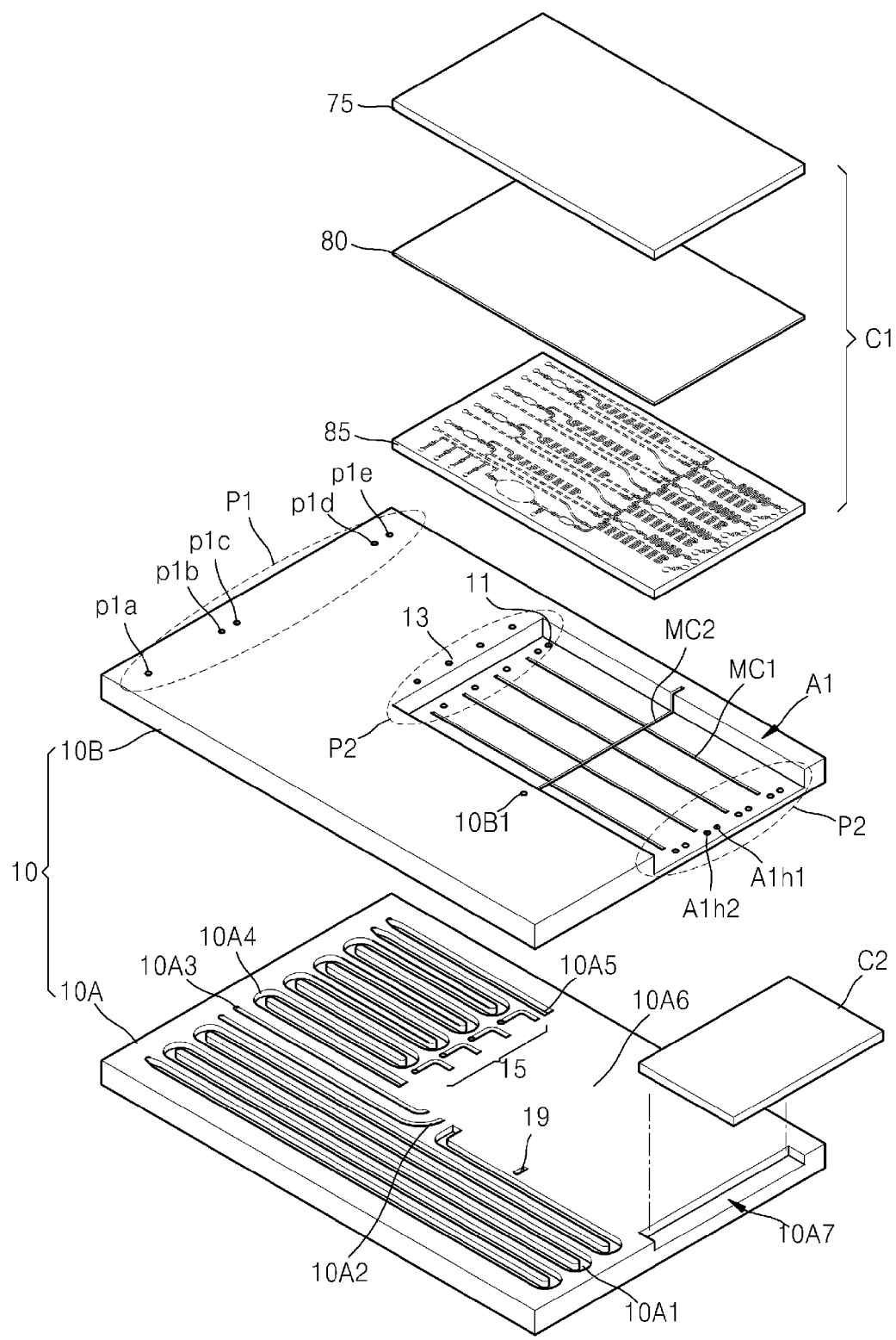
FIG. 3 is an exploded perspective detailed view of components of the gene analysis apparatus of FIG. 2.
Figure 4:
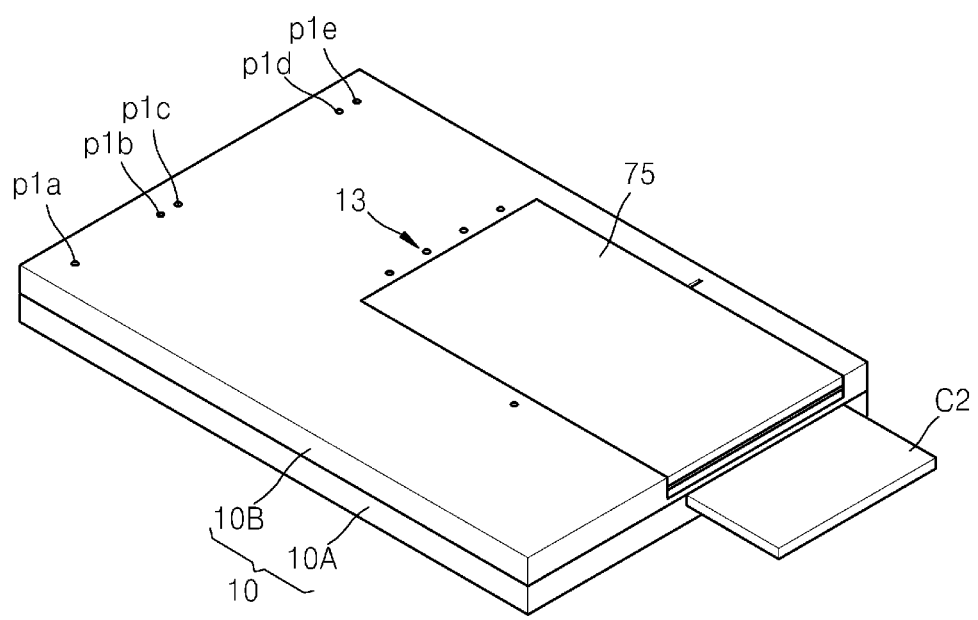
FIG. 4 is a perspective view of a gene analysis apparatus packaged by combining a sample preparation chip, a package layer, and a polymerase chain reaction ("PCR") chip illustrated in FIG. 3.

FIG. 3 is an exploded perspective detailed view of components of the gene analysis apparatus 100 of FIG. 2.

Referring to FIG. 3, the sample preparation chip C1 may include a fluidic layer 85, a membrane layer 80, and a pneumatic layer 75 sequentially stacked in the sample preparation chip C1 in this stated order. A thickness of the fluidic layer 85 may be, for example, about 0.7 millimeter (mm). The membrane layer 80 may be an elastomer layer. In one embodiment, for example, the membrane layer 80 may include polydimethylsiloxane ("PDMS"). The membrane layer 80 may be completely non-transmissive or partially transmissive to a liquid or a gas. A thickness of the membrane layer 80 may be, for example, about 0.25 mm. The pneumatic layer 75 may be connected to an external pneumatic device. Through the pneumatic layer 75, a pressure applied to a particular portion of the membrane layer 80 may be increased or decreased so as to open or close a microvalve of a microchannel formed in the fluidic layer 85. Also, by the increasing or decreasing of the pressure, beads placed in the cell lysis chamber of the fluidic layer 85 may be periodically or non-periodically moved. A thickness of the pneumatic layer 75 may be, for example, about 0.7 mm.

The package layer 10 may include a main layer 10A and a cover 10B which covers the main layer 10A. A thickness of the main layer 10A may be, for example, about 3 mm. A thickness of the cover 10B may be, for example, about 2.65 mm. The cover 10B has a first region A1 which is recessed from an upper surface of the cover 10B to a predetermined depth. The sample preparation chip C1 may be on the first region A1. A depth of the first region A1 may be substantially equal to a thickness of the sample preparation chip C1. First and second microchannels MC1 and MC2 are in the first region A1. The first and second microchannels MC1 and MC2 may function as a passage through which air generated when a sample (e.g., nucleic acid) is prepared and quantified in the sample preparation chip C1 and when PCR is performed in the PCR chip C2, is discharged. The first microchannel MC1 includes four sub-channels aligned in parallel, and the second microchannel MC2 is perpendicular to the first microchannel MC1.

The first region A1 includes a second portion P2 which contacts the PCR chip C2. The second portion P2 includes a plurality of holes which extend in a thickness direction of the cover 10B. The second portion P2 of the first region A1 is considered as within the recess and directly adjacent to the recess, as illustrated by the dotted line in FIG. 3. In this regard, the holes are distanced from first ends of sub-channels of the first microchannel MC1. Each one of the sub-channels of the first microchannel MC1 corresponds to two holes at the first ends. The holes at the first ends of the sub-channels in the second portion P2 may form the channel 12 between the sample preparation chip C1 and the PCR chip C2. A plurality of holes may also be further in the recess near second ends which oppose the first ends of the sub-channels of the first microchannel MC1, and also in a first portion P1 outside the first region A1.

Among the holes in the recess within the second portion P2 of the first region A1, five holes are near the second ends of the sub-channels of the first microchannel MC1 in the first region A1. Among the five holes, four holes respectively correspond to other holes (not shown) of the first region A1. The remaining hole 11 may function as a passage through which waste is discharged from the fluidic layer 85 to the main layer 10A. The four holes in the recess within the second portion P2 at the second end (excluding hole 11) of the first region A1 may function as a passage through which a sample, a reagent for preparing a sample, and air flow from the main layer 10A to the fluidic layer 85.

Each of four holes 13 in the second portion P2 but outside the recess of the first region A1 may function as a passage through which a PCR mixture is supplied from a PCR mixture chamber (not shown) placed outside to a PCR mixture supply channel 15 of the main layer 10A.

Also, holes are in the first portion P1 separate from the second portion P2 of the cover 10B. In detail, the first portion P1 has five holes, namely, first through fifth holes p1a, p1b, p1c, p1d, and p1e, each of which is spaced apart from each other is connected to a particular region of the main layer 10A. The first through fifth holes p1a through p1e are respectively connected to first through fifth regions 10A1 through 10A5 of the main layer 10A. A hole 10B1 is near the first region A1 of the cover 10B. The hole 10B1 is a discharge hole through which waste is discharged.

The hole 10B1 is aligned with and corresponds to an end of a microchannel 19 of the main layer 10A. A waste flows to the microchannel 19 from the fluidic layer 85. A hole (not shown) that corresponds to the opposing other end of the microchannel 19 is in the first region A1. The hole corresponds to a hole at an outlet of a bead chamber of the fluidic layer 85.

The main layer 10A has a sixth region 10A6 corresponding to the first region A1 of the cover 10B, and a seventh region 10A7 in which a portion of the PCR chip C2 is mounted. A surface of the sixth region 10A6 is even, that is substantially coplanar and continuous. The seventh region 10A7 is recessed from an upper surface of the main layer 10A. A step is formed between the sixth and seventh regions 10A6 and 10A7. A height of the step may be equal to a thickness of the PCR chip C2. First through fifth regions 10A1 through 10A5 of the main layer 10A are near the sixth region 10A6. The first through fifth regions 10A1 through 10A5 of the main layer 10A are concave regions which extend from the upper surface of the main layer 10A and include a bottom surface which is lower than the upper surface of the main layer 10A. The first through fifth regions 10A1 through 10A5 are apart from each other.

The first region 10A1 may be a winding region or a region where a sample of a biomaterial to be examined is stored. The sample of the biomaterial may be supplied to a first end of the first region 10A1 through the first hole p1a. An end of the first region 10A1 is connected to a cell lysis chamber in the fluidic layer 85 through holes (not shown) in the cover 10B and a hole in the fluidic layer 85 of the sample preparation chip C1. The first region 10A1 may have a volume that is suitable for housing, for example, 1 milliliter (ml) of a sample. Alternatively, the first region 10A1 may have a volume that is suitable for housing 1 ml or less, or 1 ml or greater of a sample. When the first region 10A1 is formed, a volume of the first region 10A1 may be controllable according to a width and a depth of the first region 10A1. Volumes of the second through fifth regions 10A2-10A5 may also be controllable in the same way as described above.

The second region 10A2 is a region to which a lysis buffer flows. The lysis buffer is supplied to a first end of the second region 10A2 of the main layer 10A through the second hole p1b. The lysis buffer in the second region 10A2 is supplied to the cell lysis chamber of the fluidic layer 85 at the opposing second other end of the second region 10A2 through a hole in the cover 10B and a hole in the fluidic layer 85. The lysis buffer may be supplied due to an external pressure. The lysis buffer may include a non-specific cell lysis agent or a specific cell lysis agent. A non-specific cell lysis agent may include, for example, at least one selected from the group consisting of a surfactant, NaOH, and a chaotropic salt. A specific cell lysis agent may be, for example, a lysozyme, a penicillin, or a beta-lactam-based antibiotic agent.

The third region 10A3 may be a region to which external dried air is supplied. The dried air flows into a first end of the third region 10A3 of the main layer 10A through the third hole p1c of the first portion P1 of the cover 10B, and the dried air may be supplied to the cell lysis chamber of the fluidic layer 85 through the third region 10A3, a hole in the cover 10B, and a hole in the fluidic layer 85.

The fourth region 10A4 of the main layer 10A is a region to which a washing solution is supplied. The washing solution is supplied due to an external pressure, and supplied to a first end of the fourth region 10A4 of the main layer 10A through the fourth hole p1d of the first portion P1 of the cover 10B. The washing solution in the fourth region 10A4 may be supplied to the cell lysis chamber of the fluidic layer 85 through a hole in the cover 10B at the opposing second other end of the fourth region 10A4. The washing solution may be water, a buffer (for example, a PBS buffer), or saline.

The fifth region 10A5 is a region to which waste is supplied from the sample preparation chip C1. The waste may be supplied to a first end of the fifth region 10A5 of the main layer 10A through the hole 11 of the second portion P2 of the cover 10B, and a hole of the fluidic layer 85 corresponding to the hole 11. The waste in the fifth region 10A5 is supplied to an external waste chamber through the fifth hole p1e of the first portion P1 of the cover 10B at the opposing second other end of the fifth region 10A5. In the main layer 10A, locations of the first through fifth regions 10A1 through 10A5 may be relative to each other.

FIG. 5 is a schematic view of the gene analysis apparatus 200 according to another embodiment of the present invention.

Referring to FIG. 5, a sample preparation chip C1 and a PCR chip C2 are mounted on a package layer 20 in the same direction, that is, on a same side or surface of the package layer 20. In the illustrated embodiment, for example, the sample preparation chip C1 and the PCR chip C2 are both disposed under the package layer 20. The sample preparation chip C1 is spaced apart from the PCR chip C2 in a direction parallel to the package layer 20. A partial portion of the PCR chip C2 may extend outside the package layer 20 and be exposed outside edges of the package layer 20. A channel 14 is in a portion of the package layer 20 between the sample preparation chip C1 and the PCR chip C2. The channel 14 may include a plurality of sub-channels. Through the channel 14, a fluid flows between the sample preparation chip C1 and the PCR chip C2. As described above, the sample preparation chip C1 and the PCR chip C2 are in the same direction with respect to the package layer 20. Thus, when the sample preparation chip C1 and the PCR chip C2 are mounted on the package layer 20, a single force may be applied to the sample preparation chip C1 and the PCR chip C2 that are in the same direction. Thus, the sample preparation chip C1 and the PCR chip C2 may be strongly attached to the package layer 20 so the sample preparation chip C1 and the PCR chip C2 are tightly sealed.

Figure 6:
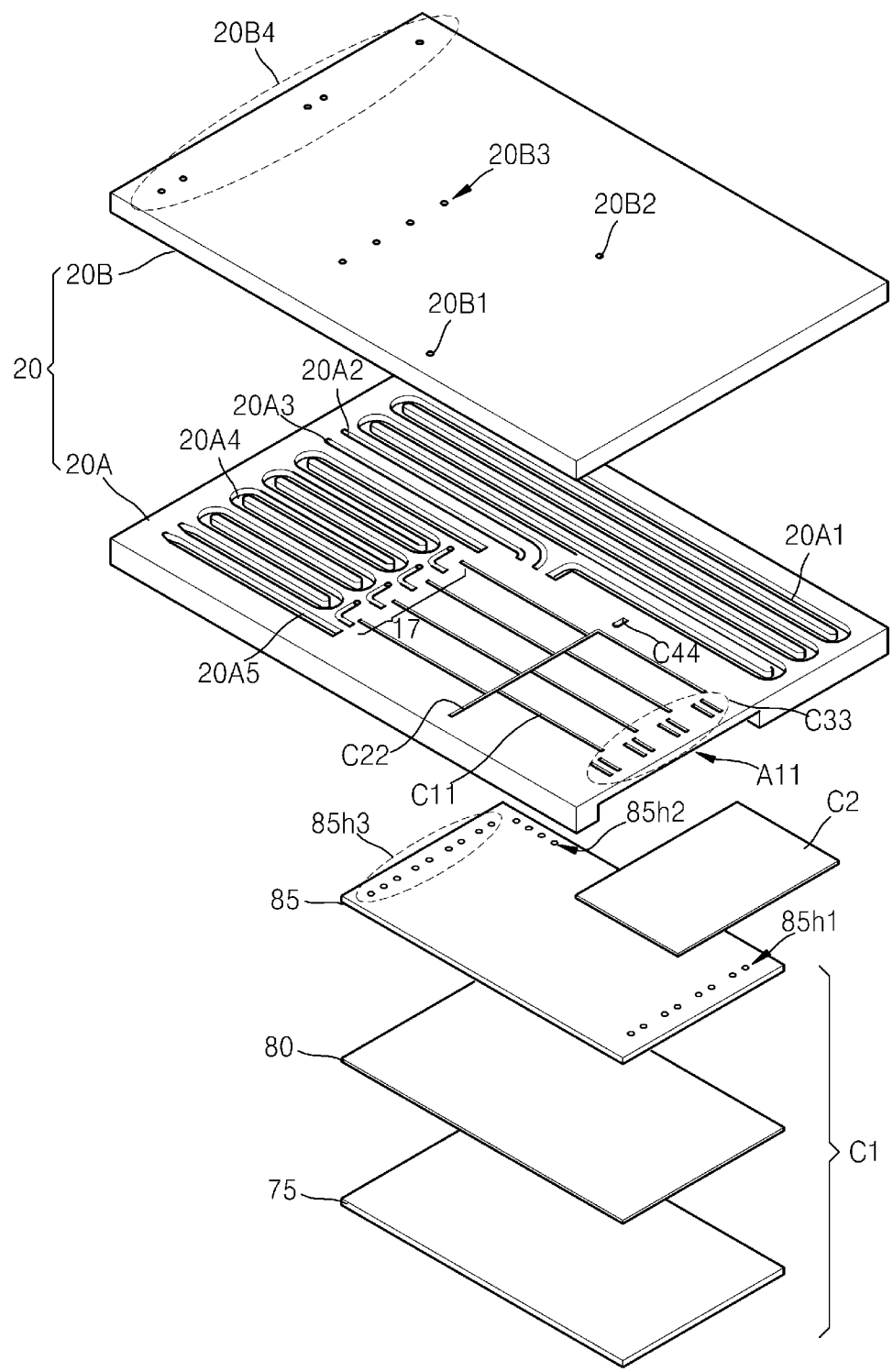
FIG. 6 is an exploded perspective detailed view of components of the gene analysis apparatus of FIG. 5.

FIG. 6 is an exploded perspective detailed view of components of the gene analysis apparatus 200 of FIG. 5.

Referring to FIG. 6, the package layer 20 may include a cover 20B and a main layer 20A. A thickness of the main layer 20A may be, for example, about 3.15 mm. A thickness of the cover 20B may be, for example, about 1 mm. The cover 20B covers (e.g., overlaps) a surface of the main layer 20A. The sample preparation chip C1 and the PCR chip C2 are mounted on another surface facing the surface of the main layer 20A. The sample preparation chip C1 and the PCR chip C2 are both disposed under the main layer 20A. Hereinafter, for ease of convenience, the surface of the main layer 20A will be referred to as an upper surface and the facing surface will be referred to as a lower surface.

The upper surface of the main layer 20A has first through fifth regions 20A1 through 20A5 corresponding to the first through fifth regions 10A1 through 10A5 of the package layer 10 of FIG. 3. In addition, a PCR mixture supply channel 17 corresponds to the PCR mixture supply channel 15 illustrated in FIG. 3. First and second microchannels C11 and C22 are in a region of the upper surface of the main layer 20A corresponding to the sample preparation chip C1. The first and second microchannels C11 and C22 correspond to the first and second microchannels MC1 and MC2 illustrated in FIG. 3. Eight third microchannels C33 are in the upper surface of the main layer 20A facing the PCR mixture supply channel 17, with the first microchannel C11 between the third microchannels C33 and the PCR mixture supply channel 17, and function as a channel through which air is discharged when a fluid flows between the fluidic layer 85 of the sample preparation chip C1 and the PCR chip C2. The PCR chip C2 may include four PCR chambers. In this regard, each of the PCR chambers corresponds to two third microchannels C33.

A recess region A1 is in the lower surface of the main layer 20A. The first through third microchannels C11, C22, and C33 are disposed above and overlapping the recess region A11. The sample preparation chip C1 and the PCR chip C2 are mounted in the recess region A11. The sample preparation chip C1 may have a first group of holes 85h1.

Figure 7:
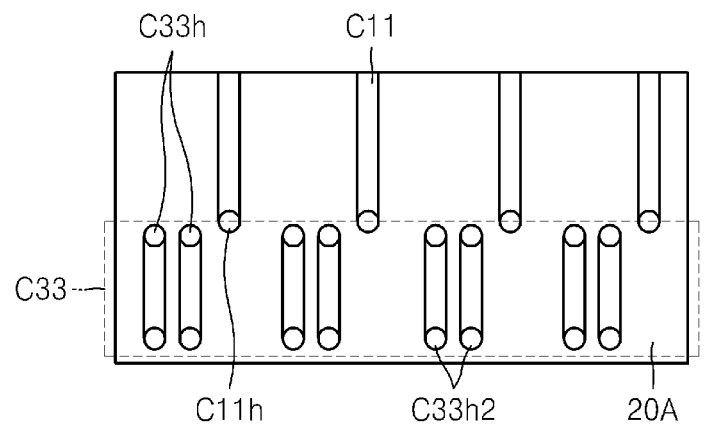
FIG. 7 is an enlarged plan view of a third microchannel and a surrounding portion thereof illustrated in FIG. 6.
Figure 8:
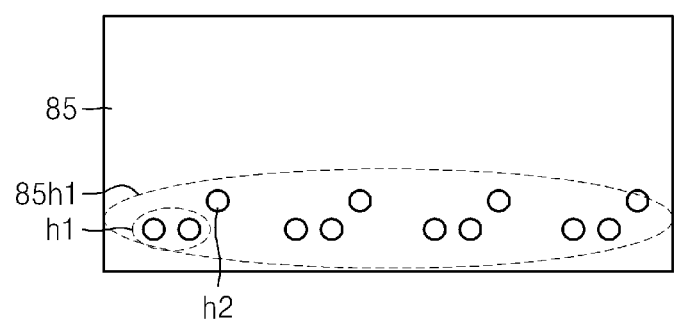
FIG. 8 is an enlarged plan view of a portion of the gene analysis apparatus of FIG. 6 including a first group of holes of a fluidic layer.

The following description will be presented with reference to FIG. 7 that is an enlarged plan view of a portion including the third microchannels C33 illustrated in FIG. 6, and FIG. 8 that is an enlarged plan view of a portion of the fluidic layer 85 including first group of holes 85h1 of the portion fluidic layer 85. Among the first group of holes 85h1, pairs of first holes h1 correspond to holes C33h at ends of the third microchannels C33 of the main layer 20A, that is, ends of the third microchannels C33 near the first microchannels C11, and second holes h2, between the pairs of first holes h1 such that one second hole h2 is between two neighboring pairs of first holes h1, correspond to holes C11h at ends of the first microchannels C11, that is, ends of the first microchannels C11 near the third microchannels C33.

The fluidic layer 85 also has a second group of holes 85h2. The second group of holes 85h2 includes four holes. The second group of holes 85h2 corresponds to holes at ends of the first through fourth regions 20A1 through 20A4 of the main layer 20A, that is, ends of the first through fourth regions 20A1 through 20A4 near the first microchannels C11. Accordingly, a sample of a biomaterial, dried air, a lysis buffer, and a washing solution are supplied from the first through fourth regions 20A1 through 20A4 through the second group of holes 85h2.

The fluidic layer 85 also has a third group of holes 85h3. The third group of holes 85h3 may include, for example, nine holes. One of the holes corresponds to the end of the fifth region 20A5 of the main layer 20A, and the remaining eight holes are paired, and the pairs of two holes correspond to holes at ends of the first microchannel C11 of the main layer 20A and holes at ends of the PCR mixture supply channel 17 corresponding to the ends of the first microchannel C11.

When the sample preparation chip C1 is mounted on the recess region A11 of the main layer 20A, the first through third groups of holes 85h1, 85h2, and 85h3 are accurately matched and/or aligned with the corresponding holes of the main layer 20A as described above. When the PCR chip C2 is mounted on the recess region A11 of the main layer 20A, one (see C33h2 of FIG. 7) of each pair of the holes at the ends of the first microchannels C33 of the main layer 20A may be matched with an inlet of the PCR chip C2 and the other one may be matched with an outlet of the PCR chip C2.

The cover 20B has a first through fourth holes 20B1 through 20B4. The first hole 20B1 corresponds to an end of the second microchannel C22 of the main layer 20A. Accordingly, the first hole 20B1 is a discharge hole through which waste is discharged through the second microchannel C22. The first hole 20B1 is connected to a waste chamber (not shown). The second hole 20B2 corresponds to an end of a fourth microchannel C44 of the main layer 20A. The second hole 20B2 is a discharge hole through which a discharge that is discharged from the fluidic layer 85 of the sample preparation chip C1 and flows into the fourth microchannel C44 is discharged. The second hole 20B2 may also be connected to the waste chamber. The third hole 20B3 includes four holes. The four third holes 20B3 respectively correspond to the other ends of four PCR mixture supply channels 17. A PCR mixture contained in four PCR mixture chambers disposed outside flows into the PCR mixture supply channel 17 of the main layer 20A through the third hole 20B3. The fourth hole 20B4 includes five holes. Among the five fourth holes 20B4, two fourth holes 20B4 correspond to ends of the fourth and fifth regions 20A4 and 20A5 of the main layer 20A. Another two fourth holes 20B4 correspond to ends of second and third regions 20A2 and 20A3 of the main layer 20A. The remaining fourth hole 20B4 corresponds to an end of the first region 20A1.

Figure 9:
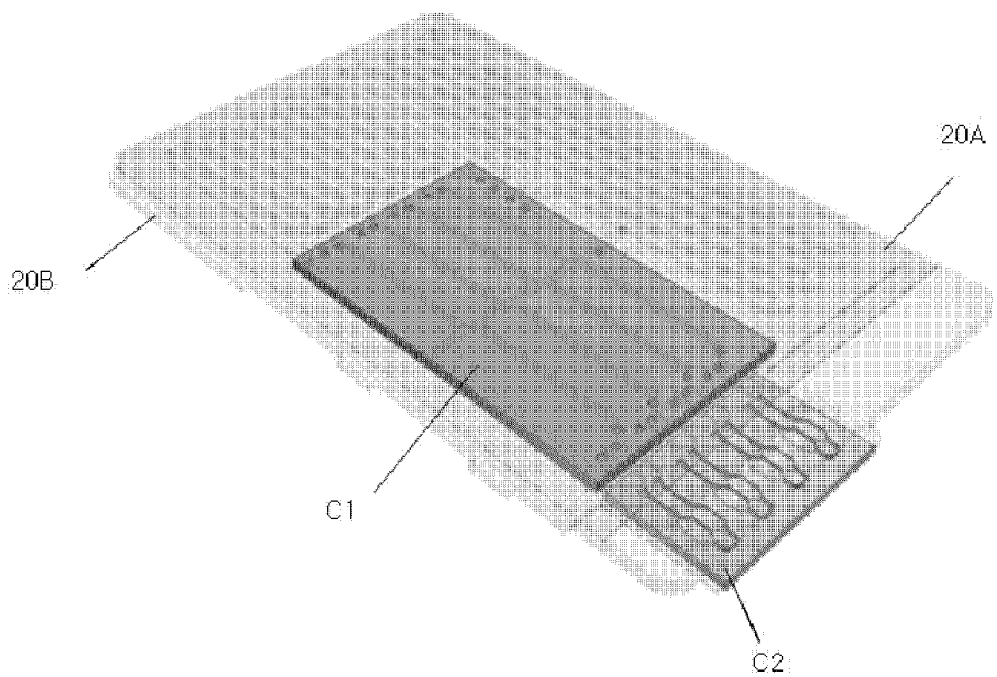
FIG. 9 is a perspective view of a gene analysis apparatus packaged by combining a sample preparation chip, a package layer, and a PCR chip illustrated in FIG. 6.

FIG. 9 is a packaged structure of the package layer 20, the sample preparation chip C1, and the PCR chip C2 illustrated in FIG. 6.

Figure 10:
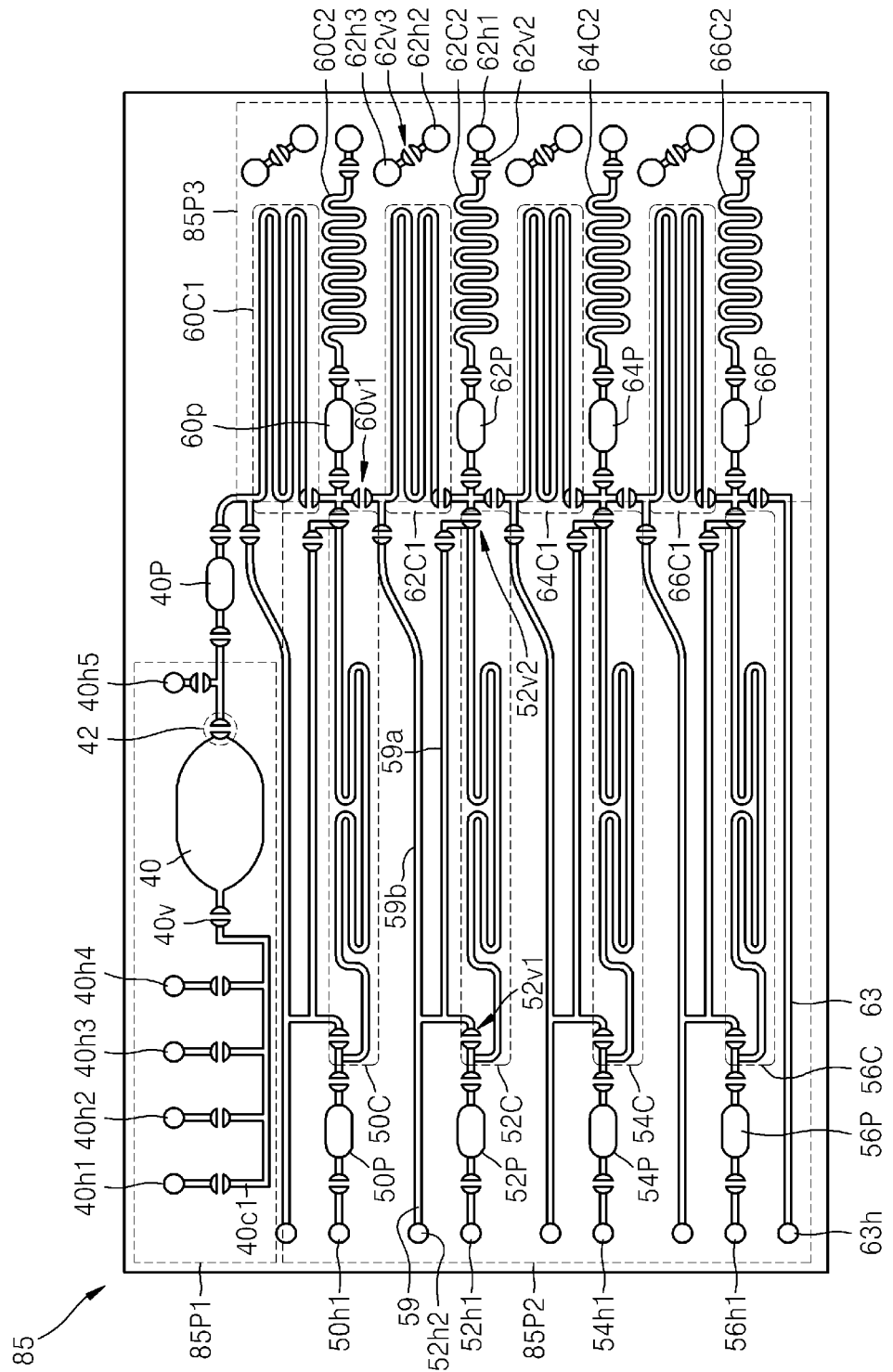
FIG. 10 is a plan view of an example of a fluidic layer of a sample preparation chip of a gene analysis apparatus according to an embodiment of the present invention.

FIG. 10 is an example of the fluidic layer 85 of the sample preparation chip C1 of a gene analysis apparatus according to an embodiment of the present invention. However, the fluidic layer 85 is not limited to the structure illustrated in FIG. 10.

Referring to FIG. 10, the fluidic layer 85 includes a first portion 85P1 which lyses a cell of a biomaterial to be examined, a second portion 85P2 which quantifies an amplification reagent, and a third portion 85P3 which mixes the fluids of the first and second portions 85P1 and 85P2 and transfers the mixed fluids to the mixture to a PCR chip C2.

The first portion 85P1 includes five holes, namely, first through fifth holes 40$h$1 through 40$h$5, a microchannel 40$c$1, and a bead chamber 40. The microchannel 40$c$1 has a plurality of microvalves 40$v$. Each of the first through fourth holes 40$h$1 through 40$h$4 is connected to an inlet of the bead chamber 40 through the microchannel 40$c$1. The first through fourth holes 40$h$1 through 40$h$4 respectively correspond to the opposing other ends of the first through fourth regions 10A1 through 10A4 of the main layer 10A (see FIG. 3). The bead chamber 40 may contain a cell to be examined, dried air, a lysis buffer, a washing solution, etc. which flow in through the first through fourth holes 40$h$1 through 40$h$4. In this regard, the cell to be examined may be flow in as a cell solution. After a cell to be examined flows into the bead chamber 40, a lysis buffer may additionally flow into the bead chamber 40. Alternatively, the lysis buffer and the cell to be examined may simultaneously flow into the bead chamber 40. Also, the lysis buffer may flow into the bead chamber 40 in a mixed state with the cell to be examined. The fifth hole 40$h$5 may correspond to an end of the microchannel 19 of the main layer 10A illustrated in FIG. 3. A discharge that is generated during an operation of the bead chamber 40 is prepared, for example, a washing solution, may be discharged through the fifth hole 40$h$5.

Figure 11:
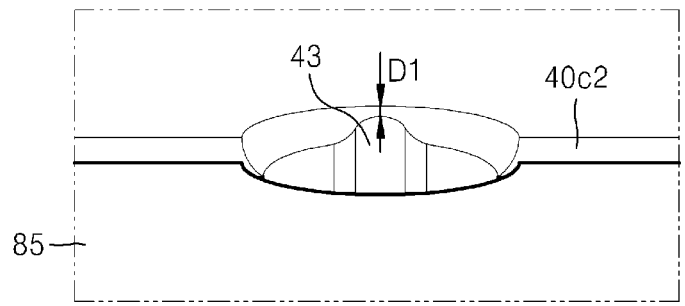
FIG. 11 is a perspective view of an example of a bead barrier illustrated in FIG. 10.

A bead barrier 42 is at an outlet of the bead chamber 40. The bead barrier 42 has a barrier member 43 connected to a microchannel 40$c$2, as illustrated in FIG. 11. The barrier member 43 is perpendicular to an extension direction of the microchannel 40$c$2. The barrier member 43 protrudes from a bottom of the microchannel 40$c$2. The barrier member 43 is lower than a top surface of the fluidic layer 85. A height difference D1 between an upper end of the barrier member 43 and the top surface of the fluidic layer 85 may be less than or equal to an average diameter of beads contained in the bead chamber 40. If the average diameter of beads is, for example, is about 20 μm, the height difference D1 may be less than 20 μm, and may be, for example, about 10 μm to about 20 μm.

Figure 12:
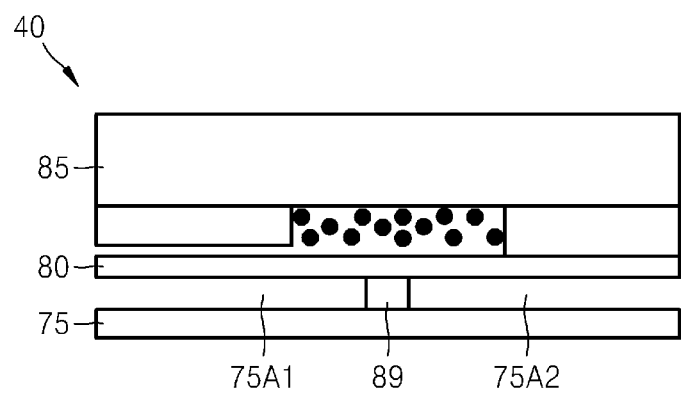
FIGS. 12 and 13 are cross-sectional views of examples of a bead chamber illustrated in FIG. 10.
Figure 13:
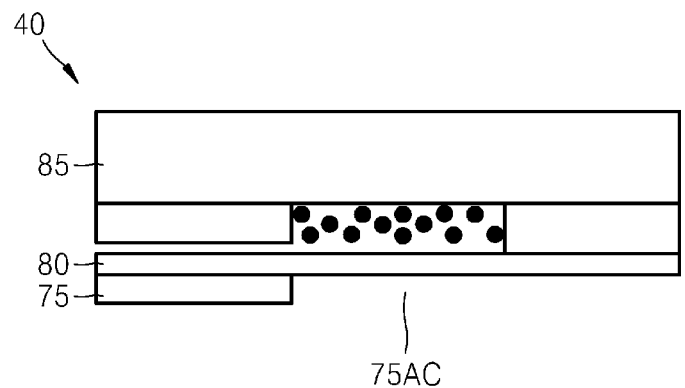

A chamber of the pneumatic layer 75, corresponding to the bead chamber 40, may include first and second chambers 75A1 and 75A2, as illustrated in FIG. 12. The first and second chambers 75A1 and 75A2 are separated from each other by a barrier wall 89. According to another embodiment, a chamber of the pneumatic layer 75, corresponding to the bead chamber 40, may be a single chamber 75AC, as illustrated in FIG. 13.

Referring to FIG. 10, the microchannel 40$c$2 disposed at the outlet of the bead chamber 40 is connected to the second and third portions 85P2 and 85P3. A pump 40P is in a microchannel between the first portion 85P1 and the third portion 85P3. The pump 40P enables transportation of a cell lysis product from the bead chamber 40 to the third portion 85P3. The second portion 85P2 includes first through fourth pumps 50P, 52P, 54P, and 56P and first through fourth metering channels 50C, 52C, 54C, and 56C respectively connected to the first through fourth pumps 50P, 52P, 54P, and 56P. The first through fourth pumps 50P, 52P, 54P, and 56P pump a PCR mixture contained in a PCR chamber through first through fourth holes 50$h$1, 52$h$1, 54$h$1, and 56$h$1 to provide the PCR mixture to the first through fourth metering channels 50C, 52C, 54C, and 56C, respectively. The first through fourth holes 50$h$1, 52$h$1, 54$h$1, and 54$h$1 correspond to the four holes in the bottom of the first region A1 among the holes in the second portion P2 of the cover 10B of FIG. 3.

Each of microchannels between the first through fourth pumps 50P, 52P, 54P, and 56P and the first through fourth holes 50$h$1, 52$h$1, 54$h$1, and 56$h$1 P has a microvalve. Each of the opposing ends of the first through fourth metering channels 50C, 52C, 54C, and 56C has a microvalve. The first through fourth metering channels 50C, 52C, 54C, and 56C have the same volume and are aligned in parallel each other. A volume of each of the first through fourth metering channels 50C, 52C, 54C, and 56C may be, for example, about 2 micro liters (μl). The volumes of the first through fourth metering channels 50C, 52C, 54C, and 56C may be controlled when the gene analysis apparatus is designed. The structure of the first through fourth metering channels 50C, 52C, 54C, and 56C may be different from the structure illustrated in FIG. 10.

Each of the first through fourth metering channels 50C, 52C, 54C, and 56C is connected to one microchannel 59, as will be described with reference to the second metering channel 52C. The microchannel 59 includes a first microchannel 59$a$ and a second microchannel 59$b$. The first microchannel 59$a$ connects a microvalve 52$v$1 at a first end of the second metering channel 52C and a microvalve 52$v$2 at the opposing second other end of the second metering channel 52C. The second microchannel 59$b$ has a second end connected next to a microvalve 60$v$1 of the second metering channel 62C1 of the third portion 85P3. The opposing first other end of the second microchannel 59$b$ is connected to a hole 52$h$2. The hole 52$h$2 is connected to the first microchannel MC1 in the bottom of the first region A1 of the cover 10B illustrated in FIG. 3. The first end of the first microchannel 59$a$ is connected between the opposing ends of the second microchannel 59$b$. The first microchannel 59$a$ is a channel through which excess mixture that remains after the second metering channel 52C is fully filled during when a PCR mixture is quantified is discharged. The second microchannel 59$b$ is open when a PCR mixture is mixed with a cell lysis product (e.g., nucleic acid) in the third portion 85P3, that is, a mixing portion.

The second portion 85P2 further includes a microchannel 63. A first end of the microchannel 63 is connected to a hole 63$h$, and the opposing second other end is connected to a second end of the fourth metering channel 56C, an inlet of a fourth pump 66P, and a rear end of a fourth metering channel 66C1 of the third portion 85P3. The opposing second other end of the microchannel 63 passes through microvalves and is connected to the end of the fourth metering channel 56C, the inlet of the fourth pump 66P, and the rear end of the fourth metering channel 66C1 of the third portion 85P3.

When the first through fourth metering channels 60C1, 62C1, 64C1, and 66C1 of the third portion 85P3 are filled with a cell lysis product, excess cell lysis product that remains after the first through fourth metering channels 60C1, 62C1, 64C1, and 66C1 are fully filled is discharged through the microchannel 63. The hole 63h connected to the end of the microchannel 63 corresponds to the hole 11 in the second portion P2 of the cover 10B of FIG. 3. Accordingly, a cell lysis product that flows in the microchannel 63 is discharged to the fifth region 10A5 of the main layer 10A of FIG. 3 through the holes 63h and 11.

The third portion 85P3 includes the first through fourth metering channels 60C1, 62C1, 64C1, and 66C1, first through fourth micropumps 60P, 62P, 64P, and 66P, and first through fourth mixing channels 60C2, 62C2, 64C2, and 66C2. The first through fourth metering channels 60C1, 62C1, 64C1, and 66C1 are respectively connected to the first through fourth micropumps 60P, 62P, 64P, and 66P via microchannels, and the first through fourth micropumps 60P, 62P, 64P, and 66P are respectively connected to the first through fourth mixing channels 60C2, 62C2, 64C2, and 66C2 via microchannels, each of which has a microvalve. The first through fourth metering channels 60C1, 62C1, 64C1, and 66C1 are filled with a cell lysis product including a nucleic acid supplied from the bead chamber 40. The first through fourth micropumps 60P, 62P, 64P, and 66P alternately pump, during each mixing process, the cell lysis product filling the first through fourth metering channels 60C1, 62C1, 64C1, and 66C1 and a PCR mixture filling the first through fourth metering channels 50C, 52C, 54C, and 56C of the second portion 85P, and then supply the cell lysis product and the PCR mixture to the first through fourth mixing channels 60C2, 62C2, 64C2, and 66C2, in which predetermined amounts of the pumped cell lysis product and the PCR mixture are pumped per one-time pumping.

Figure 14:
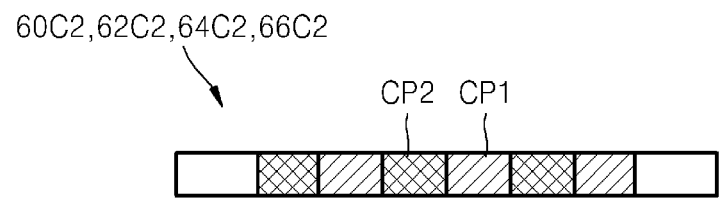
FIG. 14 is a cross-sectional view of a mixing channel illustrated in FIG. 10, in which the mixing channel is alternately filled with a cell lysis product plug and a PCR mixture plug.

FIG. 14 illustrates a cross-sectional view of a cell lysis product plug CP1 and a PCR mixture plug CP2, which are sequentially filled in each of the first through fourth mixing channels 60C2, 62C2, 64C2, and 66C2, by such pumping. By controlling an operation of each of the first through fourth micropumps 60P, 62P, 64P, and 66P, one-time pumping amount may be controlled. Accordingly, volumes of the cell lysis product plug CP1 and the PCR mixture plug CP2 may be able to be increased or reduced. In order to increase a mixing effect, the first through fourth mixing channels 60C2, 62C2, 64C2, and 66C2 wind in a plan view. A volume of each of the first through fourth mixing channels 60C2, 62C2, 64C2, and 66C2 may be, for example, about 2 μl. Volumes of the first through fourth mixing channels 60C2, 62C2, 64C2, and 66C2 may be controlled by changing a width and length of each mixing channel when the first through fourth mixing channels 60C2, 62C2, 64C2, and 66C2 are designed.

An alignment structure of the first through fourth metering channels 60C1, 62C1, 64C1, and 66C1, the first through fourth micropumps 60P, 62P, 64P, and 66P, and the first through fourth mixing channels 60C2, 62C2, 64C2, and 66C2 will be described in detail with reference to the second metering channel 62C1, the second micropump 62P, and the second mixing channel 62C2. This description may also be applied to an alignment structure of a metering channel, a micropump, and a mixing channel of the third portion 85P3. The second metering channel 62C1 winds vertically. A volume of the second metering channel 62C1 may be, for example, about 2 μl. The volume of the second metering channel 62C1 may be controlled by changing a width and length of the second metering channel 62C1 when the second metering channel 62C1 is designed. A front end of the second metering channel 62C1 is connected to a rear end of the first metering channel 60C1, an inlet of the first pump 60P, an end of the second microchannel 59a of the second portion 85P2, and an end of the first metering channel 50C of the second portion 85P2, through microchannels. Each of the microchannel connecting the front end of the second metering channel 62C1 to the rear end of the first metering channel 60C1, and the microchannel connecting the inlet of the first pump 60P to the end of the second microchannel 59a of the second portion 85P2 has a microvalve. The rear end of the second metering channel 62C1 is connected to an inlet of the second micropump 62P, a front end of the third metering channel 64C1, and an end of the second metering channel 52C of the second portion 85P2, through microchannels. Each of the microchannel connecting the rear end of the second metering channel 62C1 to the inlet of the second micropump 62P, and the microchannel connecting the front end of the third metering channel 64C1 to the end of the second metering channel 52C of the second portion 85P2 has a microvalve.

An outlet of the second pump 62P is connected to an end of the second mixing channel 62C2. The outlet of the second pump 62P is connected to a first end of the second mixing channel 62C2 via a microvalve. The opposing second other end of the second mixing channel 62C2 is connected to a hole 62h1 via a microvalve 62v2. The hole 62h1 corresponds to a hole A1h1 in the second portion P2 of the cover 10B illustrated in FIG. 3. The hole A1h1 corresponds to an inlet of a PCR chamber of the PCR chip C2. Accordingly, a mixed product in the second mixing channel 62C1 flows into the PCR chip C2 through the hole 62h1. Second and third holes 62h2 and 62h3 are near the hole 62h1. The second and third holes 62h2 and 62h3 are connected to each other via a microchannel having a microvalve 62v3. The second hole 62h2 corresponds to the hole A1h1 in the second portion P2 of the cover 10B illustrated in FIG. 3. The hole Ah1 of the cover 10B is a hole through which a solution discharged from the PCR chip C2 flows. Accordingly, a solution discharged from the PCR chip C2 flows into the fluidic layer 85 through the second hole 62h2, and flows through the microchannel between the second and third holes 62h2 and 62h3 and flows out through the third hole 62h3. The third hole 62h3 is connected to the first microchannel MC1 in the bottom of the first region A1 of the cover 10B illustrated in FIG. 3. The second pump 62P continuously pumps until a mixed product in the second mixing channel 62C1 flows to the inlet of the PCR chamber of the PCR chip C2, fills the PCR chamber, and then flows out through an outlet of the PCR chamber. Once the content flows out of the PCR chamber, the microvalves 62v2 and 62v3 are closed. By doing so, the PCR chamber is closed.

Figure 15:
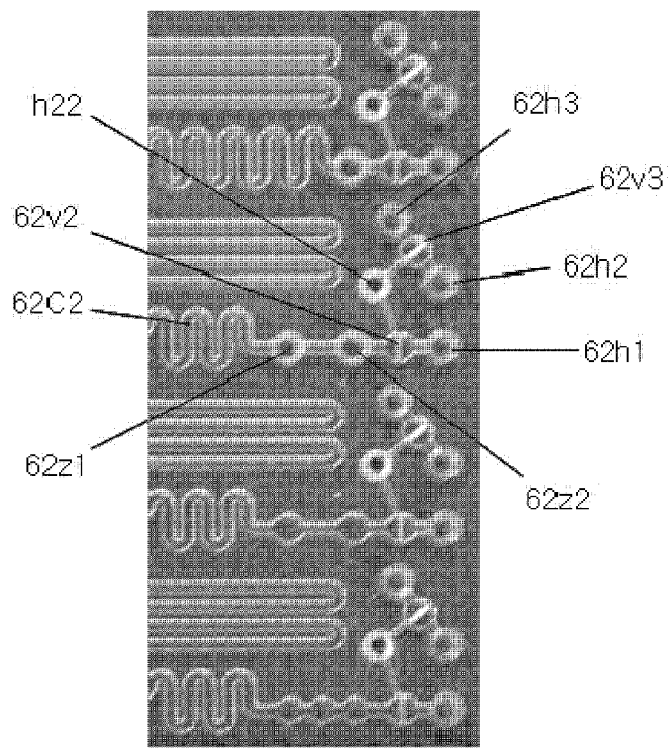
FIG. 15 is a plan view of a portion of a fluidic layer of FIG. 10, in which a bubble trap zone is between a mixing channel and a channel connected to a PCR chip.

Also, as illustrated in FIG. 15, bubble trap zones 62z1 and 62z2 may be next to the microvalve 62v2 at the opposing second other end of the second mixing channel 62C2. The bubble trap zones 62z1 and 62z2 reduce or effectively prevent bubbles from flowing into the PCR chamber C2. When the mixed product in the second mixing channel 62C2 passes the bubble trap zones 62z1 and 62z2, bubbles contained in the mixed product gather at upper portions of the bubble trap zones 62z1 and 62z2. A portion of the fluidic layer 85 corresponding to each of the bubble trap zones 62z1 and 62z2 has a hole. Accordingly, the bubble gathering in the upper portions of the bubble trap zones 62z1 and 62z2 are trapped by the holes in the fluidic layer 85. In FIG. 15, a reference numeral h22 refers to a hole in the pneumatic layer 75. By controlling a pneumatic pressure applied through the hole h22, operations of the microvalves 62v2, 62v3 are controlled.

Hereinafter, a method of quantifying a PCR mixture by using the first through fourth metering channels 50C, 52C, 54C, and 56C in the second portion 85P2 will now be described in detail. It is assumed that a depth and length of each of the first through fourth metering channels 50C, 52C, 54C, and 56C are determined to have a predetermined value. The method will be described with reference to the second metering channel 52C. An amplification reagent is loaded into the second metering channel 52C in an amount equal to or greater than a designed amount by using the second pump 52P. When the loaded amplification reagent is discharged through the opposing second other end of the second metering channel 52C, the microvalves 52-v1 and 52v2 disposed at the opposing ends of the second metering channel 52C are closed. An amplification reagent that is outside the ends of the second metering channel 52C is discharged through the microchannel 59a. By doing so, an amount of an amplification reagent that remains in the second metering channel 52C corresponds to a volume of the second metering channel 52C, thereby enabling quantification of the amplification reagent. Because the amount of the amplification reagent is accurately controlled by using the second pump 52P, an amount of an amplification reagent that is discharged through the microchannel 59a may be controlled to be a nano-level amount.

A method of quantifying a cell lysis product by using the first through fourth metering channels 60C1, 62C1, 64C1, and 66C1 in the third portion 85P3 is also performed in the similar manner as described above with reference to the first through fourth metering channels 50C, 52C, 54C, and 56C of the second portion 85P2.

In general, when a reagent is loaded into a channel, a discharge hole needs to be additionally at an opposing end of the channel opposite to the end through which the reagent is loaded. Thus, when a device or a chip is mounted on a system, an additional apparatus or structure which plugs the discharge hole is needed. However, in a gene analysis apparatus according to an embodiment of the present invention, various valves, pumps, and barriers in the fluidic layer 85 of the sample preparation chip C1 are open when external compression or decompression pressure is not applied and thus, air sufficiently flows and the respective regions of the main layer 10A do not need a additional discharge hole. Accordingly, reliability in use of a gene analysis apparatus may be increased.

The reason why valves, pumps, and barriers are open when external compression or decompression pressure is not applied lies in that a valve seat is lower than a surface of the fluidic layer 85.

Hereinafter, a gene analysis method using a gene analysis apparatus, according to an embodiment of the present invention, will be described in detail with reference to FIGS. 16 through 23. Referring to FIGS. 16 through 23, a valve to be opened is circled and a value to be closed is not circled.

Figure 16:
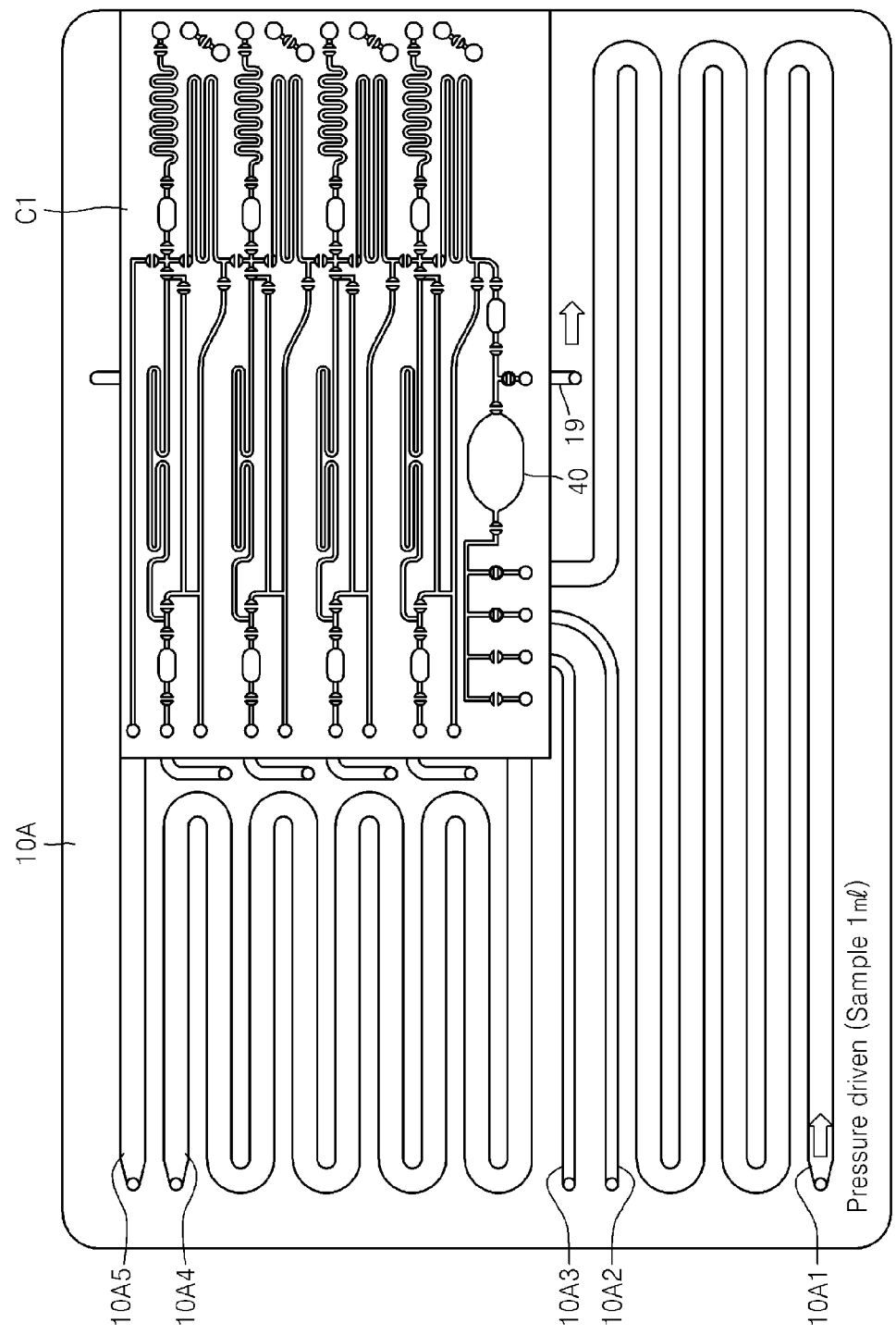
FIGS. 16 through 23 are plan views for explaining a gene analysis method using a gene analysis apparatus, according to an embodiment of the present invention.

First, as illustrated in FIG. 16, circled valves of a sample preparation chip C1 are opened, 1 ml of a sample is loaded into a bead chamber 40 through a first region of a main layer 10A of a package layer 10 by using an external pressure. The sample may correspond to a cell of a particular biomaterial. The sample in the bead chamber 40 binds to beads and the residual solution is discharged through a microchannel 19 of the main layer 10A.

Figure 17:
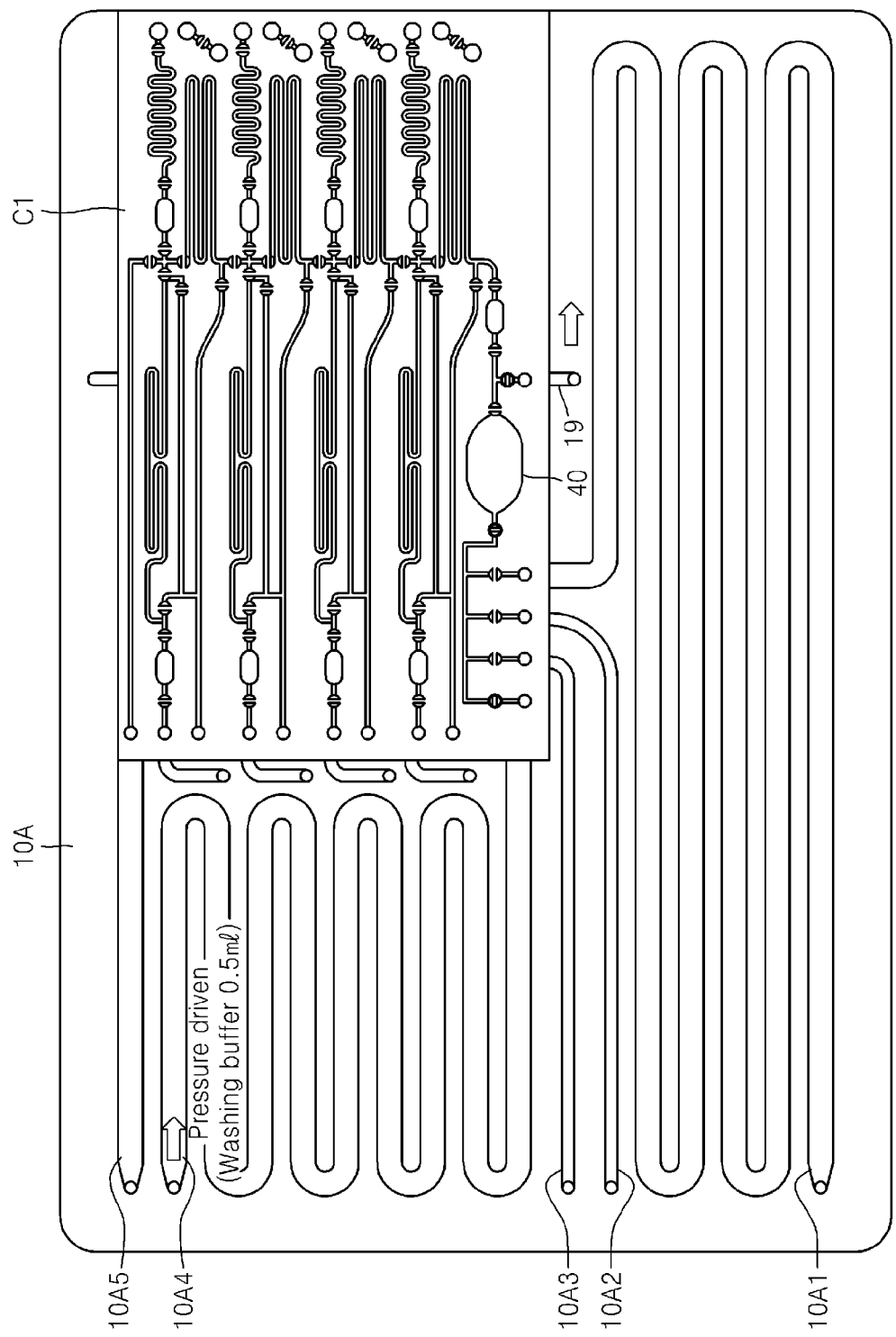

Then, as illustrated in FIG. 17, circled valves are opened, and 0.5 ml of a washing buffer is supplied to the bead chamber 40 by using external pressure. The washing buffer in the bead chamber 40 is discharged through the microchannel 19 of the main layer 10A. When the washing buffer passes the bead chamber 40, other materials than the cell binding to the beads is washed out.

Figure 18:
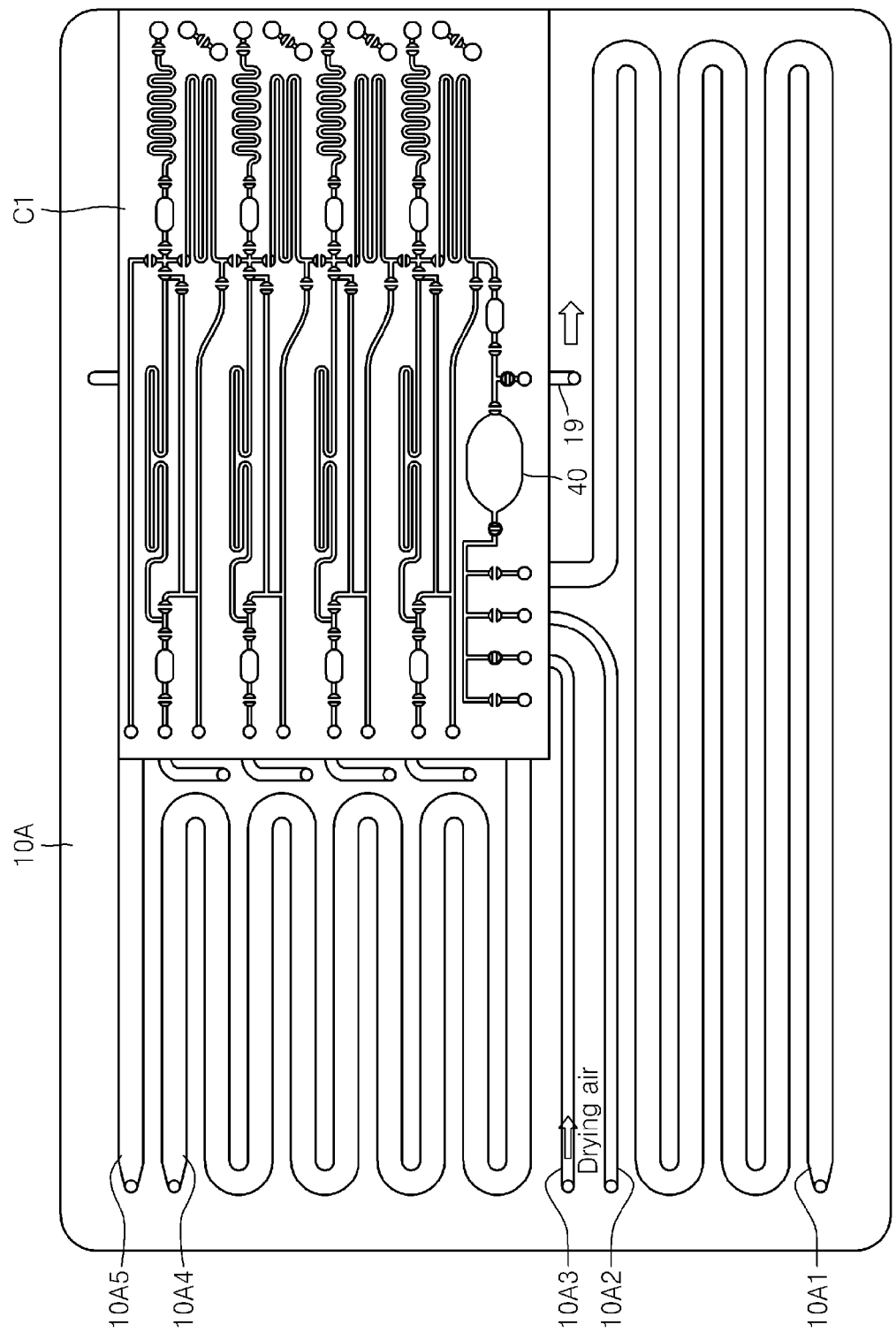

Then, as illustrated in FIG. 18, circled valves are opened, and dried air is supplied to the bead chamber 40 through a third region 10A3 of the main layer 10A. By doing so, the beads contained in the bead chamber 40 are completely dried. The supplied air is discharged through the microchannel 19 of the main layer 10A.

Figure 19:
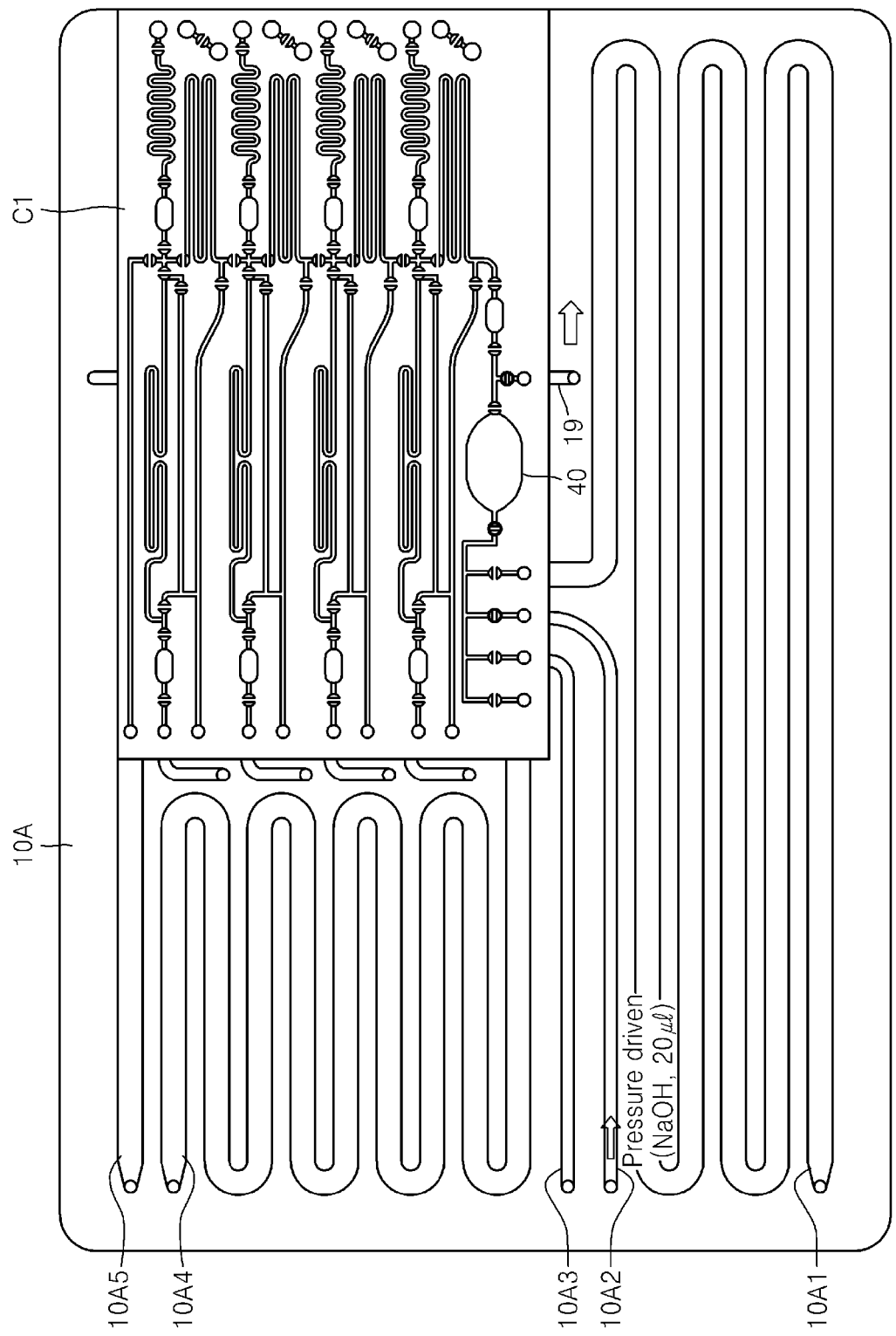

Then, as illustrated in FIG. 19, circled valves are opened, and 20 µl of sodium hydroxide (NaOH) lysis buffer is loaded into the bead chamber 40 through a second region 10A2 of the main layer 10A by using external pressure. After the lysis buffer is loaded, valves at an inlet and outlet of the bead chamber 40 are closed. A lysis buffer that is in a channel outside the bead chamber 40 is discharged through the microchannel 19 of the main layer 10A.

Figure 20:
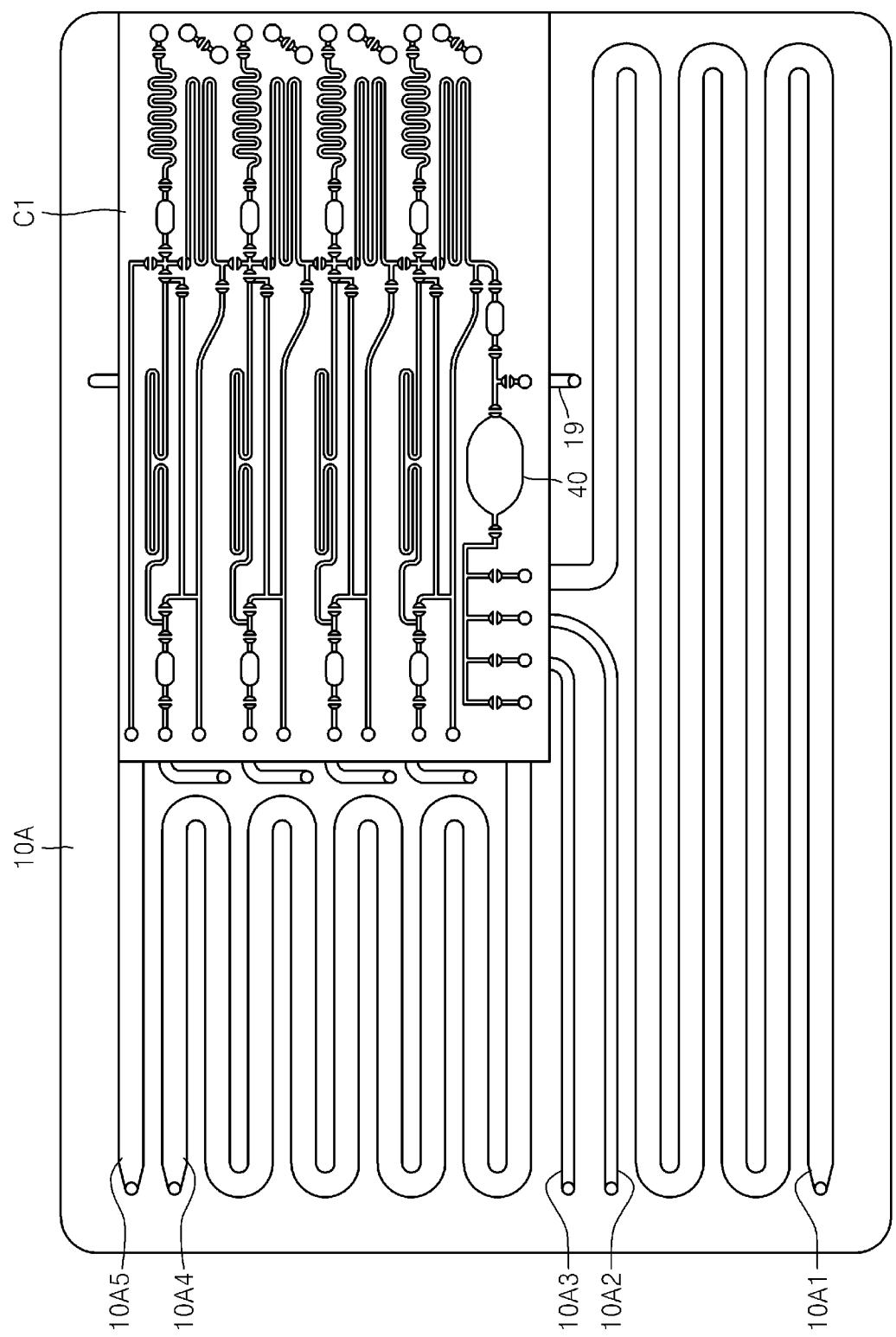

Then, as illustrated in FIG. 20, all the valves are closed, and compression or decompression is applied to a portion of a membrane corresponding to the bead chamber 40 by using a pneumatic pressure so that the beads in the bead chamber 40 periodically or non-periodically move. By doing so, lysis efficiency of cell binding the beads is increased.

Figure 21:
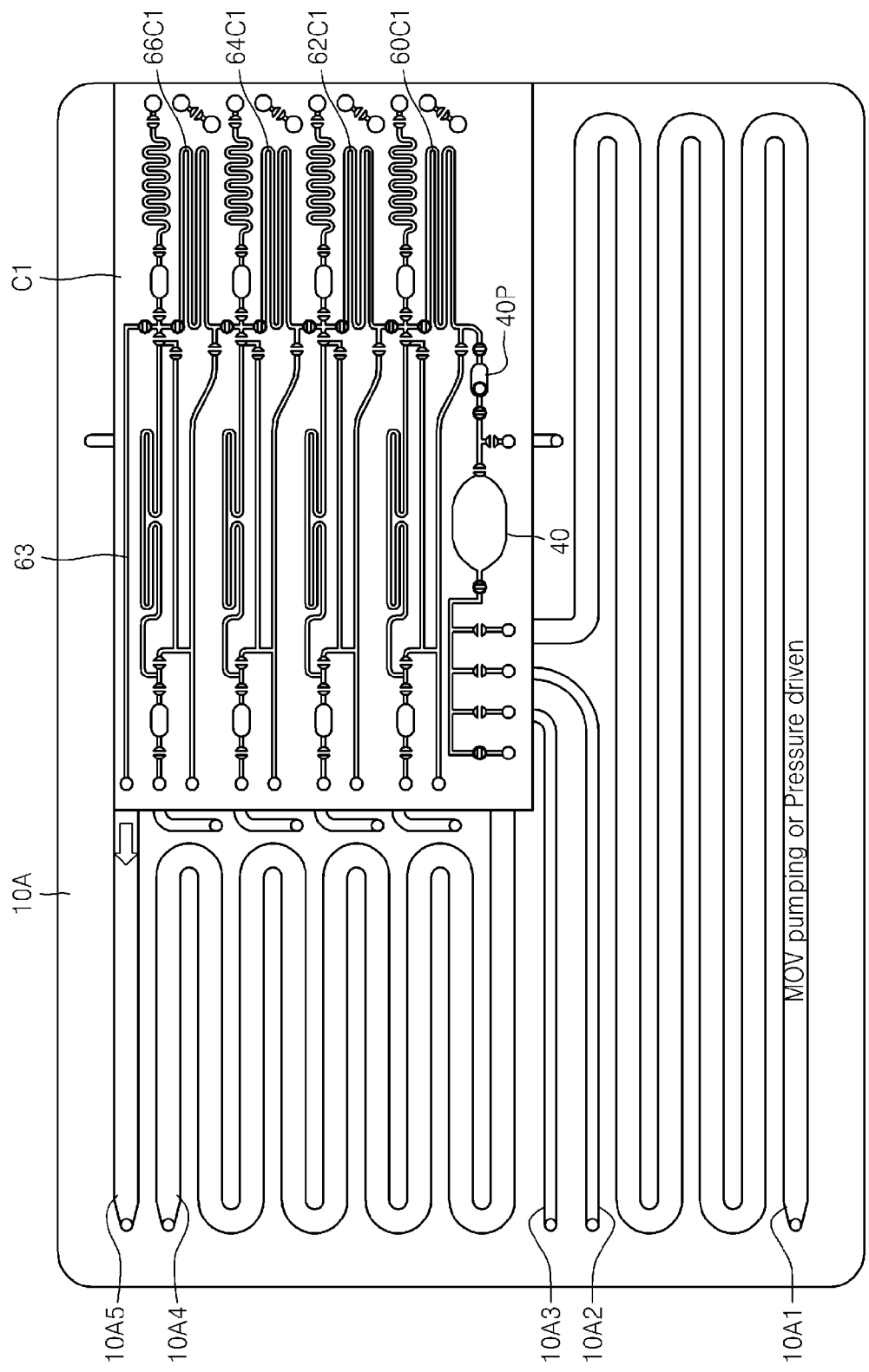

Then, as illustrated in FIG. 21, circled valves in the sample preparation chip C1 are opened, and a cell lysis product including a nucleic acid in the bead chamber 40 is moved to fill the first through fourth metering channels 60C1, 62C1, 64C1, and 66C1 by using a pump 40P in a microchannel between the bead chamber 40 and the first metering channel 60C1 or an external pressure. When the cell lysis product fills up the first through fourth metering channel 66C1, the open valves are closed. In this process, a cell lysis product that is in a microchannel 63 is discharged through the fifth region 10A5 of the main layer 10A.

Figure 22:
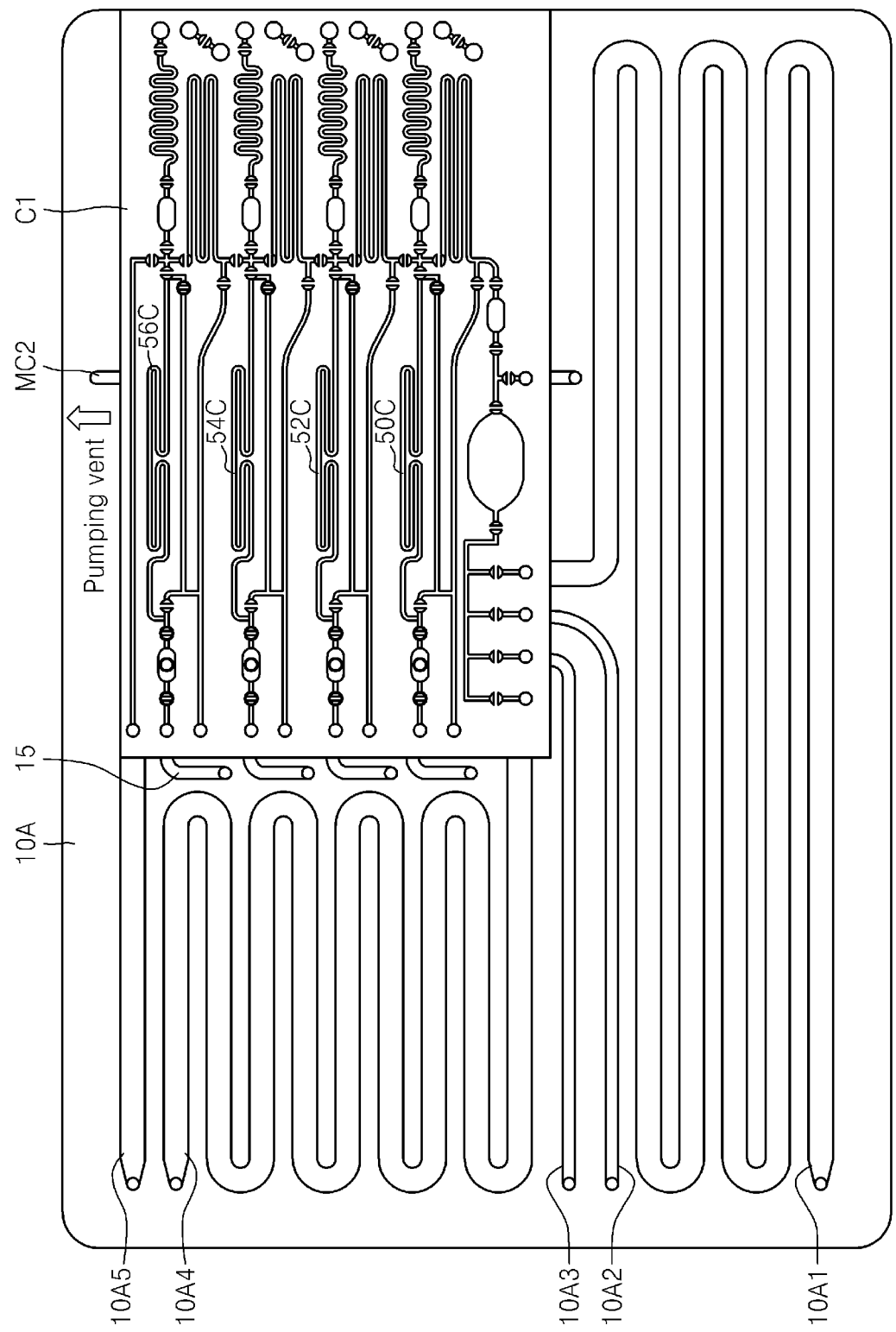

Then, as illustrated in FIG. 22, circled valves in the sample preparation chip C1 are opened, and first through fourth metering channels 50C, 52C, 54C, and 56C are filled with four different PCR mixtures through four PCR mixture supply channels 15 of the main layer 10A, respectively. In this process, excess PCR mixture that remains in other channels after the first through fourth metering channels 50C, 52C, 54C, and 56C are filled up is discharged through first and second microchannels MC1 and MC2 of the cover 10B of the package layer 10.

Figure 23:
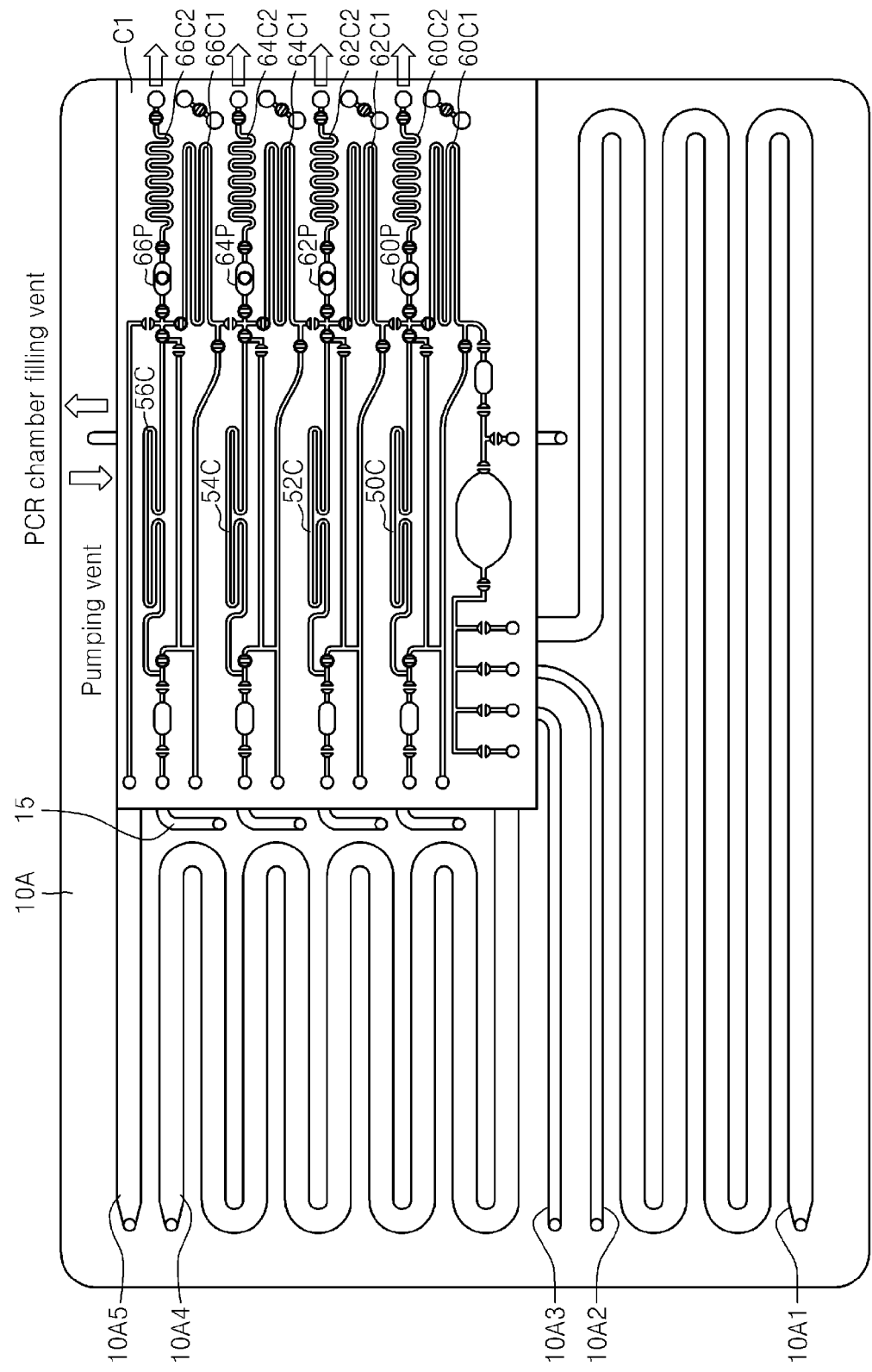

Then, as illustrated in FIG. 23, circled valves are opened, and first through fourth pumps 60P, 62P, 64P, and 66P are driven to alternately pump a solution contained in the first through fourth metering channels 50C, 52C, 54C, and 56C and a solution contained in the first through fourth metering channels 60C1, 62C1, 64C1, and 66C1, and by one-time pumping, only a predetermined amount of the solution is supplied to the first through fourth mixing channels 60C2, 62C2, 64C2, and 66C2. Such pumping continues until a PCR chamber of a PCR chip C2 is filled. When the PCR chamber is filled, PCR is performed.

As described above, when gene analysis apparatuses according to the one or more of the above embodiments of the present invention are used, a series of processes including a process of extracting of components of a cell, for example, a nucleic acid, a process of mixing the extracted nucleic acid and a PCR mixture, for example, an amplification reagent, and a process of transporting the mixed product to a PCR chamber to perform PCR may be performed in a batch process without exposure to the outside. Accordingly, contamination caused by a foreign material may be reduced or effectively prevented during the process period from extracting of a nucleic acid to performing of PCR, and thus, the entire analysis process is stably performed. Accordingly, accuracy and reliability of analysis results may be improved.

It should be understood that the embodiments described herein should be considered in a descriptive sense only and not for purposes of limitation. Descriptions of features or aspects within each embodiment should typically be considered as available for other similar features or aspects in other embodiments.

What is claimed is:

1. A gene analysis apparatus comprising:
   a sample preparation chip in which a polymerase chain reaction solution sample is prepared,
   a polymerase chain reaction chip in which polymerase chain reaction is performed on the polymerase chain reaction solution sample, and
   a package layer on which the sample preparation chip and the polymerase chain reaction chip are mounted;
   wherein the sample preparation chip comprises:
      a first metering channel in which a polymerase chain reaction mixture is quantified;
      a first channel through which a material flows into a bead chamber;
      a bead chamber containing beads and configured to lyse a cell;
      a second metering channel in which a cell lysis product supplied from the bead chamber is quantified;
      a mixing channel in which materials contained in the first and second metering channels are mixed;
      a micropump between the first metering channel and the mixing channel, and between the second metering channel and the mixing channel; and
      a second channel through which a material contained in the mixing channel flows into a channel of the package layer;
   and wherein the package layer comprises a channel in which the polymerase chain reaction solution sample flows from the sample preparation chip to the polymerase chain reaction chip; and the following regions:
      a first region for biomaterial sample storage, which connects a sample supply hole in the package layer to the bead chamber of the sample preparation chip;
      a second region for lysis buffer flow, which connects a lysis buffer supply hole in the package layer to the bead chamber of the sample preparation chip;
      a third region for supply of external air, which connects an air supply hole in the package layer to the bead chamber of the sample preparation chip;
      a fourth region for supply of a washing solution, which connects a washing solution supply hole in the package layer to the bead chamber of the sample preparation chip; and
      a fifth region for waste discharge, which connects a waste discharge hole in the package layer to a waste discharge hole in the sample preparation chip.

2. The gene analysis apparatus of claim 1, wherein the sample preparation chip and the polymerase chain reaction chip are on a same side of the package layer.

3. The gene analysis apparatus of claim 1, wherein the package layer is disposed between the sample preparation chip and the polymerase chain reaction chip.

4. The gene analysis apparatus of claim 1, wherein the package layer comprises a main layer and a cover which covers the main layer,
   wherein the main layer comprises the first region for biomaterial sample storage, second region for lysis buffer flow, third region for supply of external air, fourth region for supply of a washing solution, and fifth region for waste discharge;
   and the cover comprises the sample supply hole, lysis buffer supply hole, air supply hole, washing solution supply hole, and waste discharge hole.

5. The gene analysis apparatus of claim 1, wherein the channel in which the polymerase chain reaction solution sample flows from the sample preparation chip to the polymerase chain reaction chip comprises a plurality of sub-channels.

6. The gene analysis apparatus of claim 1, wherein the channel in which the polymerase chain reaction solution sample flows from the sample preparation chip to the polymerase chain reaction chip is a vertical or horizontal channel.

7. The gene analysis apparatus of claim 1, wherein each of the first and second metering channels and the mixing channel has a predetermined volume.

8. The gene analysis apparatus of claim 1, wherein a bubble trap zone is at an end of the mixing channel near the channel of the package layer.

9. A gene analysis method comprising:
   preparing a polymerase chain reaction sample in the sample preparation chip of the apparatus of claim 1;
   supplying the polymerase chain reaction sample to the polymerase chain reaction chip of the apparatus of claim 1; and
   performing a polymerase chain reaction on the polymerase chain reaction sample in the polymerase chain reaction chip,
   wherein the steps of preparing a polymerase chain reaction sample, supplying the polymerase chain reaction sample to the polymerase chain reaction chip, and performing a polymerase chain reaction are performed in-situ and without exposure of the polymerase chain reaction sample outside of the apparatus.

10. The method of claim 9, wherein the preparing the polymerase chain reaction solution sample comprises:
   lysing a cell;
   quantifying a cell lysis product;
   quantifying a polymerase chain reaction mixture; and
   mixing the quantified cell lysis product and the quantified polymerase chain reaction mixture.

11. The method of claim 10, wherein the quantifying a cell lysis product comprises:
   opening valves at ends of a metering channel in which the cell lysis product is filled;
   supplying the cell lysis product to the metering channel in such an amount that an amount of the cell lysis product is greater than a volume of the metering channel;
   closing the valves at the ends of the metering channel; and
   discharging the cell lysis product which is outside the metering channel.

12. The method of claim 10, wherein the lysing the cell comprises allowing the cell to move periodically or non-periodically.

13. The method of claim 10, wherein the quantifying the polymerase chain reaction mixture comprises:
   opening valves at ends of a metering channel in which the polymerase chain reaction mixture is filled;
   supplying the polymerase chain reaction mixture to the metering channel in such an amount that an amount of the polymerase chain reaction mixture is greater than a volume of the metering channel;
   closing the valves at the ends of the metering channel; and
   discharging the polymerase chain reaction mixture which is outside the metering channel.

14. The method of claim 10, wherein the mixing the quantified cell lysis product and the quantified polymerase chain reaction mixture comprises:

- alternately supplying a portion of the quantified cell lysis product and a portion of the quantified polymerase chain reaction mixture to a mixing channel.

15. The device of claim 1, wherein the device comprises a membrane layer, and a portion of the membrane is configured to move the beads in the bead chamber upon application of pneumatic pressure to the membrane.

16. The device of claim 1, wherein the sample preparation chip comprises a fluidic layer, a membrane layer, and a pneumatic layer configured to apply pressure to the membrane layer.

17. The device of claim 4, wherein the cover further comprises

- a hole connecting the first region for biomaterial sample storage to the bead chamber of the sample preparation chip;
- a hole connecting the second region for lysis buffer flow to the bead chamber of the sample preparation chip;
- a hole connecting the third region for supply of external air to the bead chamber of the sample preparation chip,
- a hole connecting the fourth region for supply of a washing solution to the bead chamber of the sample preparation chip;
- a hole connecting the fifth region for waste discharge to a waste discharge hole in the sample preparation chip.

18. The device of claim 1, wherein the PCR chip comprises a silicon layer and a glass layer.

\* \* \* \* \*